US010391042B2

(12) United States Patent
Lingoes et al.

(10) Patent No.: US 10,391,042 B2
(45) Date of Patent: Aug. 27, 2019

(54) TREATMENT COMPOSITIONS, APPARATUS AND METHODS FOR MODIFYING KERATINOUS SURFACES

(71) Applicant: The Procter & Gamble Company, Cincinnati, OH (US)

(72) Inventors: Janette Villalobos Lingoes, Cincinnati, OH (US); Thomas Elliot Rabe, Baltimore, MD (US); Grant Edward Anders Striemer, Fairfield Township, OH (US); Robert Ha, Liberty Township, OH (US); Denny Eugene Kuhlman, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 184 days.

(21) Appl. No.: 14/961,073

(22) Filed: Dec. 7, 2015

(65) Prior Publication Data

US 2017/0156994 A1 Jun. 8, 2017

(51) Int. Cl.
*A61K 8/02* (2006.01)
*A61K 8/04* (2006.01)
(Continued)

(52) U.S. Cl.
CPC ............ *A61K 8/0241* (2013.01); *A45D 34/04* (2013.01); *A45D 44/00* (2013.01); *A61K 8/044* (2013.01);
(Continued)

(58) Field of Classification Search
CPC ... B41J 2/01; B41J 2/211; B41J 2/1433; B41J 2/17; B41J 2/17593; B41J 2/2107;
(Continued)

(56) References Cited

U.S. PATENT DOCUMENTS 5,980,018 A 11/1999 Taylor et al.
6,199,973 B1 3/2001 Bartolome et al.
(Continued)

FOREIGN PATENT DOCUMENTS

DE 3906335 8/1990
DE 19534327 2/1996
(Continued)

OTHER PUBLICATIONS

PCT International Search Report with Written Opinion in corresponding international application PCT/US2016/065051 dated Feb. 9, 2017.
(Continued)

*Primary Examiner* — Manish S Shah
(74) *Attorney, Agent, or Firm* — Melissa G. Krasovec

(57) ABSTRACT

A treatment composition for, among other things, treating human skin. These compositions are stable, particulate containing, printer compositions that have one or more particulate suspending agents. The suspending agents can be present in a concentration of from about 0.1% to about 5%, by weight. The particles in the particulate composition have a combined Particle Size Distribution D50 in the range of about 200 ηm to about 500 ηm, and preferably the compositions have a zeta potential of negative 20 or less, or greater than positive 20. The particulate suspending agent is preferably a polyacrylate composition, even more preferably sodium polyacrylate. The particles can be present in a concentration of from about 1% to about 30.0%, by weight, and preferably the particles in the particulate composition have a combined Particle Size Distribution D90 of less than about 1 μm. The particulate compositions may contain $TiO_2$ particles and a second particulate composition which is an iron oxide based colorant particulate composition, another colorant particulate composition, or both.

17 Claims, 12 Drawing Sheets

(51) Int. Cl.
*A61Q 1/02* (2006.01)
*A61K 8/81* (2006.01)
*A61K 8/29* (2006.01)
*A61K 8/19* (2006.01)
*A61K 8/86* (2006.01)
*A61K 8/34* (2006.01)
*A45D 44/00* (2006.01)
*B41J 2/21* (2006.01)
*A45D 34/04* (2006.01)

(52) U.S. Cl.
CPC .................. *A61K 8/19* (2013.01); *A61K 8/29* (2013.01); *A61K 8/345* (2013.01); *A61K 8/8147* (2013.01); *A61K 8/8152* (2013.01); *A61K 8/8182* (2013.01); *A61K 8/86* (2013.01); *A61Q 1/02* (2013.01); *B41J 2/2107* (2013.01); *A45D 2044/007* (2013.01); *A61K 2800/26* (2013.01); *A61K 2800/412* (2013.01); *A61K 2800/43* (2013.01); *A61K 2800/5424* (2013.01); *A61K 2800/592* (2013.01); *A61K 2800/594* (2013.01); *A61K 2800/621* (2013.01); *A61K 2800/805* (2013.01); *A61K 2800/87* (2013.01)

(58) Field of Classification Search
CPC ...... B41J 2/1755; B41J 2/2114; B41J 2/2117; B41J 11/0015; B41J 11/002; B41J 2/2056; B41J 2/21; B41J 2/0057; B41J 3/60; B41J 2002/012; B41J 2/04598; B41J 2/04586; B41J 2/04588; B41J 2/04595; C09D 11/36; C09D 11/40; C09D 11/30; C09D 11/38; C09D 11/322; C09D 11/328; C09D 11/101; C09D 11/005; C09D 11/54; C09D 11/52; B41M 5/0011; B41M 5/0017; B41M 7/00; B41M 7/0072; B41M 5/52; B41M 5/5218
See application file for complete search history.

(56) References Cited

U.S. PATENT DOCUMENTS

| | | | |
|---|---|---|---|
| 6,312,124 B1 | 11/2001 | Esormeaux | |
| 6,531,142 B1 | 3/2003 | Rabe et al. | |
| 6,585,365 B1 * | 7/2003 | MacMillan | B41M 5/52 347/100 |
| 7,648,364 B2 | 1/2010 | Dauga | |
| 7,731,326 B2 | 6/2010 | Perez et al. | |
| 7,890,152 B2 | 2/2011 | Edgar | |
| 8,007,062 B2 | 8/2011 | Edgar | |
| 8,027,505 B2 | 9/2011 | Edgar | |
| 8,128,192 B1 | 3/2012 | Simmons | |
| 8,184,901 B2 | 5/2012 | Edgar | |
| 8,231,292 B2 | 7/2012 | Rabe | |
| 8,695,610 B2 | 4/2014 | Samain | |
| D750,225 S | 2/2016 | Rabe | |
| D750,772 S | 3/2016 | Rabe | |
| 9,616,668 B1 | 4/2017 | Rabe et al. | |
| 9,616,692 B1 | 4/2017 | Rabe et al. | |
| 9,782,971 B2 | 10/2017 | Vernon et al. | |
| 2003/0060810 A1 | 3/2003 | Syrowicz | |
| 2004/0130587 A1 | 7/2004 | Yakura et al. | |
| 2004/0181196 A1 | 9/2004 | Pickup et al. | |
| 2005/0147771 A1 * | 7/2005 | Kaneko | B41M 5/52 428/32.34 |
| 2006/0164460 A1 | 7/2006 | Uwagaki et al. | |
| 2007/0076045 A1 | 4/2007 | James et al. | |
| 2008/0194971 A1 | 8/2008 | Edgar | |
| 2008/0204503 A1 | 8/2008 | Studer et al. | |
| 2009/0025747 A1 | 1/2009 | Edgar | |
| 2010/0224205 A1 | 9/2010 | Mitra | |
| 2010/0224209 A1 | 9/2010 | Rabe | |
| 2010/0224210 A1 | 9/2010 | Rabe | |
| 2010/0224211 A1 | 9/2010 | Samain | |
| 2011/0129283 A1 | 6/2011 | Samain | |
| 2011/0155161 A1 | 6/2011 | Samain | |
| 2011/0159463 A1 | 6/2011 | Rabe | |
| 2011/0162673 A1 | 7/2011 | Samain | |
| 2011/0285765 A1 | 11/2011 | Lamontagne et al. | |
| 2012/0081421 A1 | 4/2012 | Kondo | |
| 2013/0182032 A1 * | 7/2013 | Roberts | C09D 175/04 347/20 |
| 2013/0189332 A1 * | 7/2013 | Breyfogle | A61K 8/25 424/401 |
| 2015/0298459 A1 | 10/2015 | Yasumoto et al. | |
| 2015/0360015 A1 | 12/2015 | Rabe | |
| 2015/0360016 A1 | 12/2015 | Rabe | |
| 2015/0360017 A1 | 12/2015 | Rabe | |
| 2015/0360018 A1 | 12/2015 | Baker | |
| 2015/0360019 A1 | 12/2015 | Clancy | |
| 2015/0360020 A1 | 12/2015 | Wu | |
| 2016/0022006 A1 | 1/2016 | Rabe | |
| 2016/0022008 A1 | 1/2016 | Rabe | |
| 2016/0022009 A1 | 1/2016 | Rabe | |
| 2016/0022010 A1 | 1/2016 | Rabe | |
| 2016/0022011 A1 | 1/2016 | Rabe | |
| 2016/0022972 A1 | 1/2016 | Rabe | |
| 2017/0157962 A1 | 6/2017 | Rabe et al. | |

FOREIGN PATENT DOCUMENTS

| | | | |
|---|---|---|---|
| DE | 19534327 A1 * | 2/1996 | ............. B41M 5/52 |
| FR | 2933585 B1 | 10/2011 | |
| JP | 10181002 A | 7/1998 | |
| JP | 2006297691 A | 11/2006 | |
| WO | WO2009036876 | 3/2009 | |
| WO | WO2010004531 | 1/2010 | |

OTHER PUBLICATIONS

Search Report and Written Opinion for PCT/US2016/065047 dated Mar. 31, 2017.
Search Report and Written Opinion for PCT/US2016/065048 dated Dec. 7, 2015.
International Search Report and Written Opinion for PCT/US2016/065049 dated Feb. 13, 2017.
International Search Report and Written Opinion for PCT/US2016/065050 dated Feb. 13, 2017.
All Office Actions for U.S. Appl. No. 14/960,907, filed Dec. 7, 2015.
All Office Actions for U.S. Appl. No. 14/960,949, filed Dec. 7, 2015.
All Office Actions for U.S. Appl. No. 14/960,976, filed Dec. 7, 2015.
All Office Actions for U.S. Appl. No. 14/961,047, filed Dec. 7, 2015.

* cited by examiner

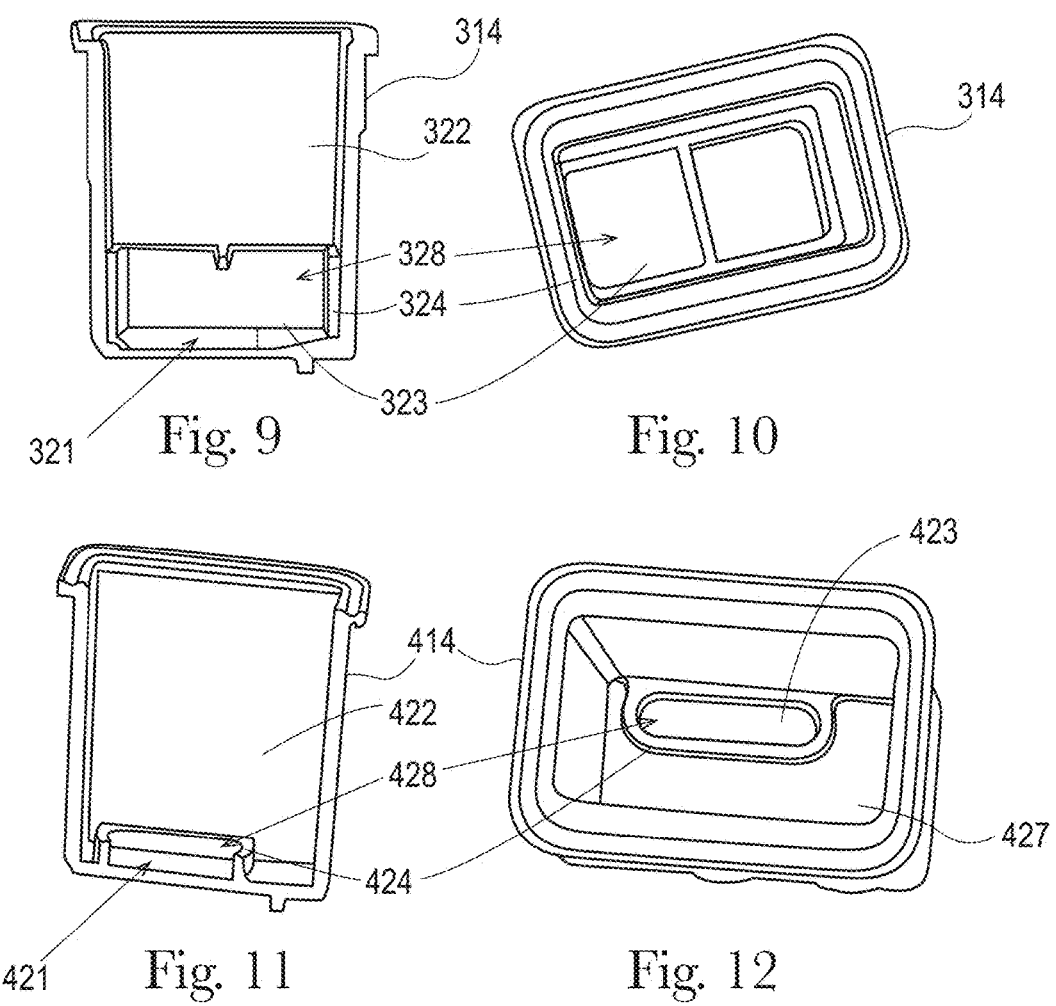

TREATMENT COMPOSITIONS, APPARATUS AND METHODS FOR MODIFYING KERATINOUS SURFACES

FIELD OF THE INVENTION

This invention relates to printable treatment compositions and an apparatus for applying compositions to skin, and other keratinous surfaces. The compositions can modify color or structure of the keratinous surface.

BACKGROUND OF THE INVENTION

Inkjet devices, particularly piezo electric and thermal, are common for both personal and industrial printing purposes. Most commonly, such devices are found in consumer homes as a means to create high quality prints and photos. In such applications the fluid inks that are commonly used for jetting onto various types of white papers utilize molecular colorants commonly known as dyes. Dyes have an advantage for such systems because they are typically more stable than pigment colorants. Pigmented, or particulate based colorants are challenging to stabilize in fluids used for jetting applications because such fluids typically require a very low fluid viscosity, most commonly less than 10 centipoise. For formulations of such low viscosity any particulates having a specific gravity greater that of the fluid carrier will have the tendency to settle over time, and this settling rate can be predicted for Newtonian fluids by Stoke's Law. Pigments are frequently used for black inkjet inks as they can be more easily stabilized by incorporating particles that are small enough, typically less than 50 nanometers, to be at least partially stabilized by Brownian motion.

If opacity, or hiding power, of the underlying substrate is a desirable property of the ink then particles of greater than 100 ηm are typically required. More specifically, particles less than 100 ηm are invisible to the human eye. The maximum efficiency of coverage is typically seen in particles greater than 200 ηm. Thus these particles will be large enough to be subject to Stokes Law. Furthermore, the material or composition of the particle is also very important as materials with higher refractive indexes will have greater hiding power. The challenge then becomes finding a high refractive index particle with a specific gravity as close as possible to common fluid carriers, usually between 0.8 and 1.2. The options are very limited and the most commonly used opacifying particles that have a refractive index greater than 2.0 also have a specific gravity greater than 2.0. In the case of titanium dioxide, the opacifier most commonly used in the paint industry, the specific gravity is 4.2, making it settle rapidly in low viscosity fluids.

For these reasons existing inks that contain high specific gravity particles like titanium dioxide are designed to be able to be re-mixable with some type of vigorous mixing, either automated or hand shaking. There are only a few examples of such inks in the marketplace, and they are all designed for industrial applications. All existing examples are delivered in a bladder type cartridge or directly from a jar/can. An example of a titanium dioxide containing white ink from Epson is the EPSON Ultrachrome® GSX White Ink Cartridge. This is used for commercial printing applications and utilizes a solvent based formulation designed for Piezo inkjet systems. The cartridge is designed with a large bladder reservoir containing the ink and requires weekly re-mixing by vigorous agitation. Another example is the Hewlett Packard Scitex white ink cartridge. This intended for use in HP Scitex series printers outfitted with an optional Scitex White Ink Upgrade Kit. The upgrade kit contains an HP White Ink Homogenizer that automatically shakes the white ink cartridge daily to keep the ink pigments in suspension. Thus current opacifying white ink cartridges are only available for industrial or commercial applications and all are designed to contain the pigment in an open reservoir type delivery system so that they are able to be re-mixed through shaking. These industrial printer examples are simply not compatible with consumer, in-home, hand held printing devices.

For example, attempts have been made at more precise, and localized application of compositions that hide, or cover-up skin deviations. Handheld devices that are moved across the skin have been developed to apply skin treatment compositions to local defects. But these devices have been plagued by a variety or technical issues including the difficulties associated with printing compositions that comprise particles as discussed above.

Therefore, there exists a need for printer compositions that contain particulate matter which can be printed on human skin, paper or any other surface. The particles must be reasonably stable in solution and easily redistributed into the solution should they settle. The particles must be big enough to be visible, but not so big that they fall out of solution quickly. And the particulate containing inks should be thin enough to be used with current printer cartridge and nozzle technology. Preferably, these particulate containing ink compositions can be used in methods and apparatuses that can quickly and precisely detect tonal and textural defects on skin. Then with equal speed and precision, apply the particulate containing ink compositions directly to the deviations. These compositions and apparatuses are defined by the present invention.

SUMMARY OF THE INVENTION

The present invention relates to a treatment composition for, among other things, treating human skin. These compositions are stable, particulate containing, printer compositions that have one or more particulate suspending agents. The suspending agents can be present in a concentration of from about 0.1% to about 5%, by weight. The particles in the particulate composition have a combined Particle Size Distribution D50 in the range of about 200 ηm (nano meters) to about 500 ηm, and preferably the compositions have a zeta potential of negative 20 or less, or greater than positive 20, preferably, negative 30 or less, or greater than 30. The particulate suspending agent is preferably a polyacrylate composition, even more preferably sodium polyacrylate. The particles can be present in a concentration of from about 1% to about 30.0%, by weight, and preferably the particles in the particulate composition have a combined Particle Size Distribution D90 of less than about 1 μm (micro meter). The particulate compositions may contain $TiO_2$ particles and a second particulate composition which is an iron oxide based colorant particulate composition, another colorant particulate composition, or both.

Further, one or more humectants in a concentration of from about 1.0% to about 50.0%, by weight; and, water may be provided. The treatment compositions of this invention are used in a printer device such as piezo electric, thermal ink jet or other drop on demand printer. The printer can be a part of an applicator having an applicator head having one or more applicator nozzles which may be in a linear array. The apparatus further has a reservoir containing the treatment composition, a sensor, and a CPU. The sensor takes an image of at least 10 μm² of skin, the CPU analyzes the image to calculate one or more localized L values of individual pixels or group of pixels of the skin. Then the CPU compares the local L value to a predetermined background L value to identify skin deviations. A skin deviation occurs where the difference between the local L and the background L, $\Delta L_M$, is greater than a predetermined $\Delta L_S$ (where "M" refers to a measured $\Delta L$ and "S" refers to a set $\Delta L$). Skin deviations are identified by this method and then treated with a treatment composition.

The present invention solves many problems with prior devices and methods. Specifically, printing an ink that lightens, rather than darkens the surface being treated. Lightening typically requires $TiO_2$ particles, or the like. Particle containing inks are typically not used in printers because they settle and sometimes pack after settling. The compositions of the present invention either slow settling to an acceptable rate, reduce packing so that the particles are resuspended easily (for example by simply turning the cartridge over), or both. Thus, printers using the present treatment compositions can lighten tonal variations on skin and other surfaces that benefit from a lighter ink.

The current invention is intended to further optimize an opacifying ink containing titanium dioxide and iron oxides so that it can be reliably used in consumer applications without the need for the vigorous agitation required of all the current opacifying ink examples designed for commercial applications. The current invention solves for opacifying ink formulations that require very little agitation in order to maintain formula homogeneity over time, thus easing the burden on the consumer of maintaining consistent print quality.

Further the speed with which a skin deviation is found and identified is critical because the applicator is continuously moving across the skin. The quicker the deviation is identified, the quicker the applicator nozzle, or nozzles can be activated. The quicker the nozzles are activated the more likely the skin treatment composition will hit the deviation precisely. This allows for the optimal coverage of the deviation, and minimal coverage on the areas of natural skin that do not need treatment. Thus, the simpler the detection algorithm is, the quicker and more precise the overall correction process is. This is a substantial improvement over more complicated, slower and less precise apparatuses and methods of the past.

BRIEF DESCRIPTION OF THE DRAWINGS

While the specification concludes with claims particularly pointing out and distinctly claiming the present invention, it is believed the same will be better understood from the following description taken in conjunction with the accompanying drawing in which:

FIGS. 9 and 10 are two views of the standpipe within a cartridge body; and FIGS. 11 and 12 are two views of the standpipe within a cartridge body.

DETAILED DESCRIPTION OF THE INVENTION

Figure 1:
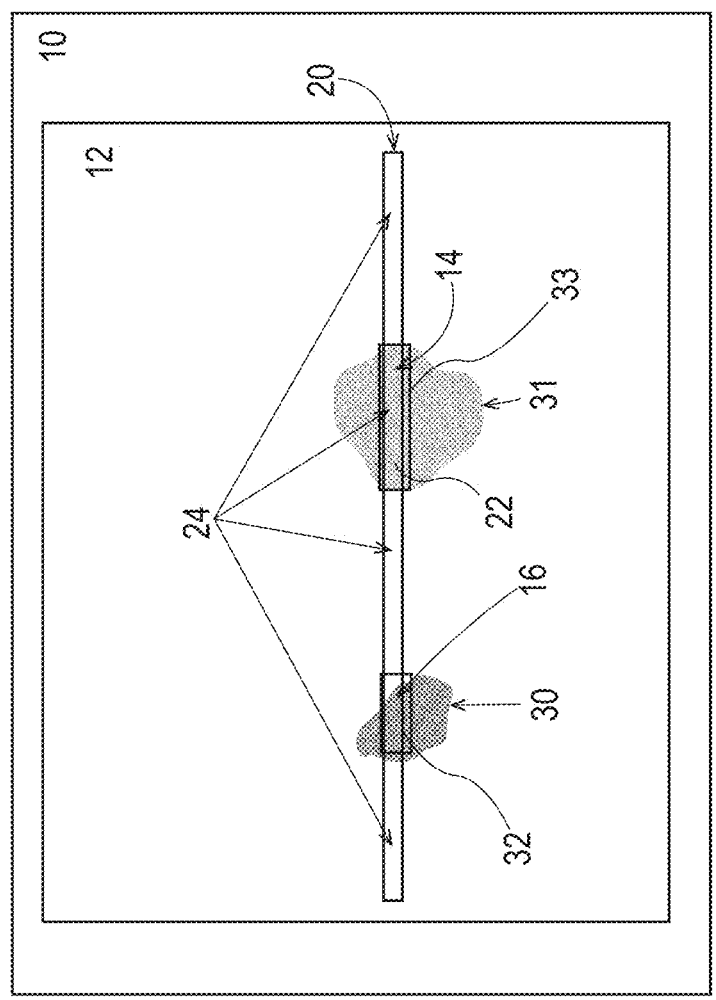
FIG. 1 is a schematic representation of an analytical window according to the present invention wherein skin is analyzed according to the methods of the present invention.

The present invention may be understood more readily by reference to the following detailed description of illustrative and preferred embodiments. It is to be understood that the scope of the claims is not limited to the specific compositions, methods, conditions, devices, or parameters described herein, and that the terminology used herein is not intended to be limiting of the claimed invention. Also, as used in the specification, including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent basis "about," it will be understood that the particular values form another embodiment. All ranges are inclusive and combinable.

Wireless communications between devices and between components within devices are known to those skilled in the art. The terms "wireless" and "wireless communications" shall mean the communication between components or devices that are accomplished by any of a variety of means including, Wireless Local Area Networks (WLAN) and Wireless Personal Area Networks (WPAN). WLAN networks use the IEEE 802.11 standards, typically known as WIFI, which is intended to replace high speed cabling with wireless communications. WPAN networks use the Bluetooth Special Interest Group standards, which are intended for wireless communication between portable equipment or fixed equipment (for example a home thermostat) and its applications. Near Field Communication (NFC) technology is another suitable wireless communication tool using standards from, for example, the NFC Forum. The apparatuses and methods of the present invention may also use wireless Radio Frequency Identification communication technology (RFID), with standards from a number of regulatory bodies, including International Organization for Standards (ISO), International Electrotechnical Commission (IEC), ASTM International, DASH7 Alliance and EPC Global. WPAN is also known as LAN (Local Area Networks) or WLAN (Wireless Local Area Networks), which is a wireless computer network that links two or more devices using a wireless distribution method within a limited area such as a home, school, office space, and the like. A piconet is a computer network which links a wireless user group of devices using Bluetooth technology protocols. For example, a piconet could include an apparatus according to the present invention connected to a smart phone or a cell phone connected to a computer, a laptop and a Bluetooth-enabled sensor, for example, a digital camera.

The term "frexel" is defined as a small pixel-like region of the keratinous surface. A frexel might correspond to a small portion of a freckle or other skin feature, or it may correspond to an area of the keratinous surface that does not have special features. The term frexel is used to suggest that what is being measured is on a 3-D surface rather than a flat surface. A region of keratinous surface is comprised of a plurality of frexels. For instance, if a resolution of 300 dots per inch (11.8 dots per mm or "dpmm") is used, a frexel may have a width and height of about ⅓₀₀th of an inch (0.085 mm) so that there are approximately 90,000 frexels per square inch (about 140 frexels per square mm). The surface of the human body may have millions of frexels.

All percentages and ratios used herein are by weight of the total composition, and all measurements made are at 25° C., unless otherwise designated.

The methods, apparatuses, and compositions of the present invention are best understood with reference to the method of use. Each of the process steps, the apparatuses and the compositions used in that step are described in turn below. The terms "device" and "apparatus" are used interchangeably throughout this specification.

TREATMENT COMPOSITIONS

The present invention may utilize a variety of treatment compositions, for example, inks, dyes, pigments, adhesives, curable compositions, optically activated compounds (for example quantum dots), metal oxides (for example, TiO2), bleaching agents, texture reducing polymers, skin care compositions, hair colorants, hair removal compositions (often referred to as depilatories), hair growth stimulants and mixtures thereof.

The treatment compositions of this invention can be delivered alone or in the presence of a dermatologically-acceptable carrier. The phrase "dermatologically-acceptable carrier", as used herein, means that the carrier is suitable for topical application to the keratinous tissue, has good aesthetic properties, is compatible with any additional components of the skin care composition, and will not cause any untoward safety or toxicity concerns. Water is by far the most common carrier, and is typically used in combination with other carriers. The carrier can be in a wide variety of forms. Non-limiting examples include simple solutions (water or oil based), emulsions, and solid forms (gels, sticks, flowable solids, amorphous materials). In certain embodiments, the dermatologically acceptable carrier is in the form of an emulsion. Emulsion may be generally classified as having a continuous aqueous phase (e.g., oil-in-water and water-in-oil-in-water) or a continuous oil phase (e.g., water-in-oil and oil-in-water-in-oil). The oil phase of the present invention may comprise silicone oils, non-silicone oils such as hydrocarbon oils, esters, ethers, and the like, and mixtures thereof. For example, emulsion carriers can include, but are not limited to, continuous water phase emulsions such as silicone-in-water, oil-in-water, and water-in-oil-in-water emulsion; and continuous oil phase emulsions such as water-in-oil and water-in-silicone emulsions, and oil-in-water-in-silicone emulsions. Additionally, the treatment composition can include for purposes of proper formulation and stabilization anti-fungal and anti-bacterial components.

The treatment composition comprises a dispersant, that can by a polyacrylate and derivatives thereof, for example poly methacrylate. The counter ion is preferably sodium, although potassium, ammonium and the like are acceptable alternatives. The dispersant typically has a molecular weight of from about 1,000 to about 20,000, as measured by standard GPC or NMR methodology known to those skilled in the art. Suitable dispersants include Darvan 811D, which is a sodium polyacrylate dispersant used in many of the Examples below, and Darvan 821A, which is an ammonium polyacrylate having a MW of about 3500.

The treatment compositions of the present invention may further comprise humectants as a carrier or chassis for the other components in the treatment composition. An exemplary class of humectants is polyhydric alcohols. Suitable polyhydric alcohols include polyalkylene glycols and alkylene polyols and their derivatives, including propylene glycol, dipropylene glycol, polypropylene glycol, polyethylene glycol and derivatives thereof; sorbitol; hydroxypropyl sorbitol; erythritol; threitol; pentaerythritol; xylitol; glucitol; mannitol; butylene glycol (e.g., 1,3-butylene glycol); pentylene glycol; hexane triol (e.g., 1,2,6-hexanetriol); glycerin; ethoxylated glycerine; and propoxylated glycerine.

Other suitable humectants include sodium 2-pyrrolidone-5-carboxylate, guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); hyaluronic acid and derivatives thereof (e.g., salt derivatives such as sodium hyaluronate); lactamide monoethanolamine; acetamide monoethanolamine; urea; sodium pyroglutamate, water-soluble glyceryl poly(meth) acrylate lubricants (such as Hispagel®) and mixtures thereof.

Inks, dyes, metal oxides and pigments (collectively referred to as "colorants" below) are used to modify the color or reflectance of the keratinous surface. These compositions are commonly used to modify color and reflectance in cosmetic, "make-up" compositions. Foundation, lipstick, eyeliner are just a few examples of these compositions, but they are all applied evenly across large portions of the keratinous surface, that is they are macro-applications. In sharp contrast, the present treatment compositions are selectively applied on a very small scale to select areas, that is, a micro application. Suitable colorants may include inorganic or organic pigments and powders. Organic pigments can include natural colorants and synthetic monomeric and polymeric colorants. Organic pigments include various aromatic types such as azo, indigoid, triphenylmethane, anthraquinone, and xanthine dyes which are designated as D&C and FD&C blues, browns, greens, oranges, reds, yellows, etc. Organic pigments may consist of insoluble metallic salts of certified color additives, referred to as the Lakes. Inorganic pigments include iron oxides, ferric ammonium ferrocyanide, manganese violet, ultramarines, chromium, chromium hydroxide colors, and mixtures thereof. The pigments may be coated with one or more ingredients that cause the pigments to be hydrophobic. Suitable coating materials that will render the pigments more lipophilic in nature include silicones, lecithin, amino acids, phospholipids, inorganic and organic oils, polyethylene, and other polymeric materials. Suitable silicone treated pigments as disclosed in U.S. Pat. No. 5,143,722. Suitable coating materials that will render the pigments more hydrophilic in nature include silica, alumina, and polyethylene glycol triethoxysilane derivatives. Inorganic white or uncolored pigments include TiO2, ZnO, ZrO2, or semiconductor quantum dots, which are commercially available from a number of sources. Other suitable colorants are identified in U.S. Pat. No. 7,166,279. Colorants are generally included at a weight percent such that the skin care composition yields a perceptible color. In one embodiment, the skin care composition exhibits a color that is perceptibly different from the color of the applicator. By perceptibly different, refers to a difference in color that is perceptible to a person having normal sensory abilities under standard lighting conditions (e.g., natural illumination as experienced outdoors during daylight hours, the illumination of a standard 100 watt incandescent white light bulb at a distance of 2 meters, or as defined by CIE D65 standard illuminate lighting at 800 lux to a 1964 CIE standard observer).

Adhesives that are compatible with keratinous surfaces are known and any such adhesive can be applied with the apparatuses of the present invention. Commercially available adhesives compatible with keratinous surfaces are available from the 3M Corporation of Minneapolis Minn. See, for example: U.S. Pat. No. 6,461,467, issued to Blatchford, et al., filed on Apr. 23, 2001; U.S. Pat. No. 5,614,310, issued to Delgado, et al., filed on Nov. 4, 1994; and U.S. Pat. No. 5,160,315, issued to Heinecke et al., filed on Apr. 5, 1991. The entire disclosures of these patent applications are incorporated by reference. After the adhesive is selectively applied to the keratinous surface, a second treatment composition can be dusted on the keratinous surface where it will stick to the adhesive. The second modification that is not adhered to the keratinous surface can then be removed leaving behind a selective, micro application of the second treatment composition. Likewise compositions that cure upon exposure to certain wavelengths of energy, infrared light for example, are known to the art and can be applied by the apparatuses of the present invention. By this method, the curable composition is selectively applied to the keratinous surface and then it is cured by exposing the keratinous surface to the curing energy source. The entire keratinous surface can be exposed, or the exposure can be done at the same time as the application.

Wrinkle or texture reducing polymers and skin tightening are known. See, for example: U.S. Pat. No. 6,139,829, issued to Estrin on Oct. 31, 2000; and US Patent Applications US20060210513A1, filed by Luizzi, et al. on Mar. 21, 2005; US20070224158A1, filed by Cassin et al. on Mar. 18, 2005; and US20070148120A1, filed by Omura et al. on Jan. 14, 2005. The entire disclosures of this patent and these published patent applications are incorporated by reference. More specifically, a cosmetic process for softening the wrinkles of wrinkled skin may comprise applying, to the wrinkled skin, a cosmetic composition, in particular an anti-wrinkle composition, comprising, in a physiologically acceptable medium suitable for topical application to the skin of the face: from 0.1 to 20% by weight of at least one tensioning agent, with respect to the total weight of the composition.

Optically-activated particles can be used as or added to the treatment compositions of this invention. Sometimes referred to a "interference pigments", these particles include a plurality of substrate particles selected from the group consisting of nylons, acrylics, polyesters, other plastic polymers, natural materials, regenerated cellulose, metals, semiconductor quantum dots and minerals; an optical brightener chemically bonded to each of the plurality of substrate particles to form integral units in the form of optically-activated particles for diffusing light. These particles help to reduce the visual perception of skin imperfections, including cellulite, shadows, skin discolorations, and wrinkles. Each of the optically-activated particles are encapsulated with a UV transparent coating to increase the diffusion of light to further reduce the visual perception of the skin imperfections. The encapsulated optically-activated particles are able to absorb ultraviolet radiation and emit visible light; and the encapsulated optically-activated particles are able to both scatter and absorb light in a diffuse manner in order to reduce the visual perception of skin imperfections, including cellulite, wrinkles, shadows, and skin discolorations, when the optically-activated particles are applied to the skin surface.

Hair colorants and hair removal compositions are also suitable for use with the apparatuses of the present invention. Likewise, skin care compositions can be applied with the apparatuses of this invention. The skin care composition may be used as, for example, a moisturizer, a conditioner, an anti-aging treatment, a skin lightening treatment, a sunscreen, a sunless tanner, and combinations thereof.

The skin care composition may comprise a safe and effective amount of one or more skin care active ("active") useful for regulating and/or improving skin condition. "Safe and effective amount" means an amount of a compound or composition sufficient to induce a positive benefit but low enough to avoid serious side effects (i.e., provides a reasonable benefit to risk ratio within the judgment of a skilled artisan). A safe and effective amount of a skin care active can be from about $1\times10^{-6}$ to about 25% by weight of the total composition, in another embodiment from about 0.0001 to about 25% by weight of the total composition, in another embodiment from about 0.01 to about 10% by weight of the total composition, in another embodiment from about 0.1 to about 5% by weight of the total composition, in another embodiment from about 0.2 to about 2% by weight of the total composition. Suitable actives include, but are not limited to, vitamins (e.g., B3 compounds such as niacinamide, niacinnicotinic acid, tocopheryl nicotinate; B5 compounds, such as panthenol; vitamin A compounds and natural and/or synthetic analogs of Vitamin A, including retinoids, retinol, retinyl acetate, retinyl palmitate, retinoic acid, retinaldehyde, retinyl propionate, carotenoids (provitamin A); vitamin E compounds, or tocopherol, including tocopherol sorbate, tocopherol acetate; vitamin C compounds, including ascorbate, ascorbyl esters of fatty acids, and ascorbic acid derivatives such as magnesium ascorbyl phosphate and sodium ascorbyl phosphate, ascorbyl glucoside, and ascorbyl sorbate), peptides (e.g., peptides containing ten or fewer amino acids, their derivatives, isomers, and complexes with other species such as metal ions), sugar amines (e.g., N-acetyl-glucosamine), sunscreens, oil control agents, tanning actives, anti-acne actives, desquamation actives, anti-cellulite actives, chelating agents, skin lightening agents, flavonoids, protease inhibitors (e.g., hexamidine and derivatives), non-vitamin antioxidants and radical scavengers, peptides, salicylic acid, hair growth regulators, anti-wrinkle actives, anti-atrophy actives, minerals, phytosterols and/or plant hormones, tyrosinase inhibitors, N-acyl amino acid compounds, moisturizers, plant extracts, and derivatives of any of the aforementioned actives. The term "derivative" as used herein refers to structures which are not shown but which one skilled in the art would understand are variations of the basic compound. For example, removing a hydrogen atom from benzene and replacing it with a methyl group. Suitable actives are further described in U.S. application publication No. US2006/0275237A1 and US2004/0175347A1.

Contrast Ratio

One method of characterizing the treatment compositions of the present invention is by its Contrast Ratio. Herein, "contrast ratio" refers to the opacity of the treatment compositions of the present invention, or the ability of the composition to reduce or prevent light transmission, determined after the composition is drawn onto an opacity chart (Form N2A, Leneta Company of Manwah, N.J. or the equivalent thereof), and by using a spectrophotometer with settings selected to exclude specular reflection. The composition is diluted with a 1% Stabylen 30 in DI water premix at a 10:1 ratio. It is applied to the top of the opacity chart and then is drawn into a film having a thickness of approximately 0.01 inches using a film applicator (e.g., as commercially available from BYK Gardner of Columbia, Md., or the equivalent thereof). The film is allowed to dry for 2 hours under conditions of 22° C.+/−1° C., 1 atm. Using a spectrophotometer, the Y tristimulus value (i.e., the XYZ color space of the film) of the product film is measured and recorded. The Y tristimulus value is measured in three different areas of the product film over the black section of the opacity chart, and also in three different areas of the product film over the white section of the opacity chart.

The contrast ratio for the treatment compositions of the present invention, is preferably from about 5 to about 35, more preferably from about 10 to about 30, and even more preferably from about 20 to about 30.

The contrast ratio is calculated as the mathematical average of the three Y tristimulus values over the black areas, divided by the mathematical average of the three Y tristimulus values over the white areas, times 100:

$$\text{Contrast Ratio} = \frac{\text{average }(Yblack)}{\text{average }(Ywhite)} \times 100$$

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

The following 10 Examples are all treatment compositions of the present inventions. They can be applied by any of the methods and apparatuses described herein, preferably, they are applied via a thermal ink jet printer head and cartridge combination.

Example 1

| | Ingredient | Description | % W/W (as added) |
|---|---|---|---|
| A | WPG75PFSP | 75% TiO2 Slurry in Propylene Glycol/Water | 22.50 |
| A | WPG45GYSP | 45% Iron Oxide Slurry Propylene Glycol/Water | 3.30 |
| A | WPG55GRSP | 45% Iron Oxide Slurry Propylene Glycol/Water | 0.20 |
| B | Water | Water | 39.00 |
| B | Propylene Glycol | Propylene Glycol | 12.50 |
| B | PVP/VA 735W | 50% VP/VA Copolymer in water | 1.50 |
| B | Symdiol | Hexanediol/Caprylyl Glycol | 1.00 |
| C | Water | Water | 10.00 |
| D | Darvan 811D | 5% Sodium Polyacrylate in water | 10.00 |
| | | Total | 100.00 |

To make the treatment composition of Example 1, first combine ingredients of Phase A in an appropriate premix container. Add the ingredients of Phase B into the main container. Mill using an IKA T25 Tekmar mill at a low speed until mixture is homogenous. While milling, add Phase A to Phase B. Add Phase C (water wash) to the premix container and add it to the main container while continuing to mill. Increase milling to high speed and mill for 15 min. Add Phase D to the main container while continuing to mill. Mill for an additional 2-3 minutes to ensure homogeneity then pour into a container, label, and store at ambient conditions.

Example 2

| | Ingredient | Description | % W/W (as added) |
|---|---|---|---|
| A | WPG75PFSP | 75% TiO2 Slurry in Propylene Glycol/Water | 22.50 |
| A | WPG45GYSP | 45% Iron Oxide Slurry Propylene Glycol/Water | 3.30 |
| A | WPG55GRSP | 45% Iron Oxide Slurry Propylene Glycol/Water | 0.20 |
| B | Water | Water | 46.00 |
| B | Propylene Glycol | Propylene Glycol | 12.50 |
| B | PVP/VA 735W | 50% VP/VA Copolymer in water | 1.50 |
| B | Symdiol | Hexanediol/Caprylyl Glycol | 1.00 |
| C | Water | Water | 10.00 |
| D | Darvan 811D | 5% Sodium Polyacrylate in water | 3.00 |
| | | Total | 100.00 |

To make the treatment composition of Example 2, first combine ingredients of Phase A in an appropriate premix container. Add the ingredients of Phase B into the main container. Mill using an IKA T25 Tekmar mill at a low speed until mixture is homogenous. While milling, add Phase A to Phase B. Add Phase C (water wash) to the premix container and add it to the main container. Increase milling to high speed and mill for 15 min. Add Phase D to the main container while continuing to mill. Mill for an additional 2-3 minutes to ensure homogeneity then pour into a container, label, and store at ambient conditions.

Example 3

| | Ingredient | Description | % W/W (as added) |
|---|---|---|---|
| A | WPG75PFSP | 75% TiO2 Slurry in Propylene Glycol/Water | 22.50 |
| A | WPG45GYSP | 45% Iron Oxide Slurry Propylene Glycol/Water | 3.30 |
| B | Water | Water | 55.59 |
| B | Propylene Glycol | Propylene Glycol | 5.00 |
| B | PVP/VA 735W | 50% VP/VA Copolymer in water | 1.50 |
| B | Symdiol | Hexanediol/Caprylyl Glycol | 1.00 |
| C | SIH RED No. 211P | Iron Oxides C.I. 77491 and Silica | 0.11 |

| Ingredient | Description | % W/W (as added) |
|---|---|---|
| D Water | Water | 10.00 |
| E Darvan 811D | 5% Sodium Polyacrylate in water | 1.00 |
| | Total | 100.00 |

To make the treatment composition of Example 3, first combine ingredients of Phase A in an appropriate premix container. Add the ingredients of Phase B into the main container. Mill using an IKA T25 Tekmar mill at a low speed until mixture is homogenous. While milling, add Phase C to Phase B. Increase milling to high speed and mill for 5 min. Continue to mill and add Phase A to the main container (Phase B+C). Mill at high speed for 15 min. Add Phase D (water wash) to the premix container and add it to the main container while continuing to mill. Add Phase E to the main container while continuing to mill. Mill for an additional 2-3 minutes to ensure homogeneity then pour into a container, label, and store at ambient conditions.

Example 4

| | Ingredient | Description | % W/W (as added) |
|---|---|---|---|
| A | WPG75PFSP | 75% TiO2 Slurry in Propylene Glycol/Water | 22.50 |
| A | WPG45GYSP | 45% Iron Oxide Slurry Propylene Glycol/Water | 3.30 |
| B | Water | Water | 48.09 |
| B | Propylene Glycol | Propylene Glycol | 12.50 |
| B | PVP/VA 735W | 50% VP/VA Copolymer in water | 1.50 |
| B | Symdiol | Hexanediol/Caprylyl Glycol | 1.00 |
| C | SIH RED No. 211P | Iron Oxides C.I. 77491 and Silica | 0.11 |
| D | Water | Water | 10.00 |
| E | Darvan 811D | 5% Sodium Polyacrylate in water | 1.00 |
| | | Total | 100.00 |

To make the treatment composition of Example 4, first combine ingredients of Phase A in an appropriate premix container. Add the ingredients of Phase B into the main container. Mill using an IKA T25 Tekmar mill at a low speed until mixture is homogenous. While milling, add Phase C to Phase B. Increase milling to high speed and mill for 5 min. Continue to mill and add Phase A to the main container (Phase B+C). Mill at high speed for 15 min. Add Phase D (water wash) to the premix container and add it to the main container while continuing to mill. Add Phase E to the main container while continuing to mill. Mill for an additional 2-3 minutes to ensure homogeneity then pour into a container, label, and store at ambient conditions.

Example 5

| | Ingredient | Description | % W/W (as added) |
|---|---|---|---|
| A | WPG75PFSP | 75% TiO2 Slurry in Propylene Glycol/Water | 22.50 |
| A | WPG45GYSP | 45% Iron Oxide Slury Propylene Glycol/Water | 3.30 |
| B | Water | Water | 30.59 |
| B | Propylene Glycol | Propylene Glycol | 30.00 |
| B | PVP/VA 735W | 50% VP/VA Copolymer in water | 1.50 |
| B | Symdiol | Hexanediol/Caprylyl Glycol | 1.00 |
| C | SIH RED No. 211P | Iron Oxides C.I. 77491 and Silica | 0.11 |
| D | Water | Water | 10.00 |
| E | Darvan 811D | 5% Sodium Polyacrylate | 1.00 |
| | | Total | 100.00 |

To make the treatment composition of Example 5, first combine ingredients of Phase A in an appropriate premix container. Add the ingredients of Phase B into the main container. Mill using an IKA T25 Tekmar mill at a low speed until mixture is homogenous. While milling, add Phase C to Phase B. Increase milling to high speed and mill for 5 min. Continue to mill and add Phase A to the main container (Phase B+C). Mill at high speed for 15 min. Add Phase D (water wash) to the premix container and add it to the main container while continuing to mill. Add Phase E to the main container while continuing to mill. Mill for an additional 2-3 minutes to ensure homogeneity then pour into a container, label, and store at ambient conditions.

Example 6

| | Ingredient | Description | % W/W (as added) |
|---|---|---|---|
| A | WPG75PFSP | 75% TiO2 Slurry in Propylene Glycol/Water | 22.50 |
| A | WPG45GYSP | 45% Iron Oxide Slury Propylene Glycol/Water | 3.30 |
| B | Water | Water | 30.59 |
| B | Propylene Glycol | Propylene Glycol | 30.00 |
| B | PVP/VA 735W | 50% VP/VA Copolymer in water | 1.50 |
| B | Symdiol | Hexanediol/Caprylyl Glycol | 1.00 |
| C | SIH RED No. 211P | Iron Oxides C.I. 77491 and Silica | 0.11 |
| D | Water | Water | 10.00 |
| E | Darvan 811D | 5% Sodium Polyacrylate | 1.00 |
| | | Total | 100.00 |

To make the treatment composition of Example 6, first combine ingredients of Phase A in an appropriate premix container. Add the ingredients of Phase B into the main container. Mill using an IKA T25 Tekmar mill at a low speed until mixture is homogenous. While milling, add Phase C to Phase B. Increase milling to high speed and mill for 5 min. Continue to mill and add Phase A to the main container (Phase B+C). Mill at high speed for 15 min. Add Phase D (water wash) to the premix container and add it to the main container while continuing to mill. Add Phase E to the main container while continuing to mill. Mill for an additional 2-3 minutes to ensure homogeneity then pour into a container, label, and store at ambient conditions. pH was adjusted with 20% citric acid to 7.0-7.5.

Example 7

| | Ingredient | Description | % W/W (as added) |
|---|---|---|---|
| A | WPG75PFSP | 75% TiO2 Slurry in Propylene Glycol/Water | 12.80 |

-continued

| | Ingredient | Description | % W/W (as added) |
|---|---|---|---|
| A | WPG45GYSP | 45% Iron Oxide Slurry Propylene Glycol/Water | 16.00 |
| B | Water | Water | 26.325 |
| B | Propylene Glycol | Propylene Glycol | 30.00 |
| B | PVP/VA 735W | 50% VP/VA Copolymer in water | 1.50 |
| B | Symdiol | Hexanediol/Caprylyl Glycol | 1.00 |
| C | SIH RED No. 211P | Iron Oxides C.I. 77491 and Silica | 0.11 |
| D | Water | Water | 10.00 |
| E | Darvan 811D | 5% Sodium Polyacrylate | 1.00 |
| | | Total | 100.00 |

To make the treatment composition of Example 7, first combine ingredients of Phase A in an appropriate premix container. Add the ingredients of Phase B into the main container. Mill using an IKA T25 Tekmar mill at a low speed until mixture is homogenous. While milling, add Phase C to Phase B. Increase milling to high speed and mill for 5 min. Continue to mill and add Phase A to the main container (Phase B+C). Mill at high speed for 15 min. Add Phase D (water wash) to the premix container and add it to the main container while continuing to mill. Add Phase E to the main container while continuing to mill. Mill for an additional 2-3 minutes to ensure homogeneity then pour into a container, label, and store at ambient conditions.

Example 8

| | Ingredient | Description | % W/W (as added) |
|---|---|---|---|
| A | WPG75PFSP | 75% TiO2 Slurry in Propylene Glycol/Water | 12.80 |
| A | WPG45GYSP | 45% Iron Oxide Slurry Propylene Glycol/Water | 16.00 |
| B | Water | Water | 26.325 |
| B | Propylene Glycol | Propylene Glycol | 30.00 |
| B | PVP/VA 735W | 50% VP/VA Copolymer in water | 1.50 |
| B | Symdiol | Hexanediol/Caprylyl Glycol | 1.00 |
| C | SIH RED No. 211P | Iron Oxides C.I. 77491 and Silica | 1.375 |
| D | Water | Water | 10.00 |
| E | Darvan 811D | 5% Sodium Polyacrylate | 1.00 |
| | | Total | 100.00 |

To make the treatment composition of Example 8, first combine ingredients of Phase A in an appropriate premix container. Add the ingredients of Phase B into the main container. Mill using an IKA T25 Tekmar mill at a low speed until mixture is homogenous. While milling, add Phase C to Phase B. Increase milling to high speed and mill for 5 min. Continue to mill and add Phase A to the main container (Phase B+C). Mill at high speed for 15 min. Add Phase D (water wash) to the premix container and add it to the main container while continuing to mill. Add Phase E to the main container while continuing to mill. Mill for an additional 2-3 minutes to ensure homogeneity then pour into a container, label, and store at ambient conditions. pH was adjusted with 20% citric acid to 7.0-7.5.

Example 9

| | Ingredient | Description | % W/W (as added) |
|---|---|---|---|
| A | SIH TiO2 R250 | TiO2, Silica, and Aluminum Hydroxide | 18.05 |
| A | SIH Yellow No. 602P | Iron Oxides C.I. 77492 and Silica | 0.40 |
| A | SIH RED No. 211P | Iron Oxides C.I. 77491 and Silica | 0.00 |
| B | Water | Water | 55.55 |
| B | Propylene Glycol | Propylene Glycol | 12.50 |
| B | PVP/VA 735W | 50% VP/VA Copolymer in water | 1.50 |
| B | Symdiol | Hexanediol/Caprylyl Glycol | 1.00 |
| B | Darvan 811D | 5% Sodium Polyacrylate | 1.00 |
| C | Water | Water | 10.00 |
| | | Total | 100.00 |

To make the treatment composition of Example 9, first combine ingredients of Phase B into the main container. Mill using an IKA T25 Tekmar mill at a low speed until mixture is homogenous. Increase milling to high speed and add ingredients of Phase A one at a time. Continue to mill and add Phase C to the main container. Mill at high speed for 15 min. Mill for an additional 2-3 minutes to ensure homogeneity then pour into a container, label, and store at ambient conditions.

Example 10

| | Ingredient | Description | % W/W (as added) |
|---|---|---|---|
| A | SIH TiO2 R250 | TiO2, Silica, and Aluminum Hydroxide | 9.60 |
| A | SIH Yellow No. 602P | Iron Oxides C.I. 77492 and Silica | 7.20 |
| A | SIH RED No. 211P | Iron Oxides C.I. 77491 and Silica | 1.37 |
| B | Water | Water | 55.83 |
| B | Propylene Glycol | Propylene Glycol | 12.50 |
| B | PVP/VA 735W | 50% VP/VA Copolymer in water | 1.50 |
| B | Symdiol | Hexanediol/Caprylyl Glycol | 1.00 |
| B | Darvan 811D | 5% Sodium Polyacrylate | 1.00 |
| C | Water | Water | 10.00 |
| | | Total | 100.00 |

To make the treatment composition of Example 10, first combine ingredients of Phase B into the main container. Mill using an IKA T25 Tekmar mill at a low speed until mixture is homogenous. Increase milling to high speed and add ingredients of Phase A one at a time. Continue to mill and add Phase C to the main container. Mill at high speed for 15 min. Mill for an additional 2-3 minutes to ensure homogeneity then pour into a container, label, and store at ambient conditions.

A summary of the ten Examples is given in Table 1 below. Included in this summary are the particulate types and concentrations, the dispersant type and level, the pH, particle size distribution, and the Opacity.

TABLE 1

| Ex. | | | | PG | Darvan 811D (as added) | Darvan 811D (active) | pH | PSD in nm D10 | D50 | D90 | Contrast Ratio |
|---|---|---|---|---|---|---|---|---|---|---|---|
| | WPG75 PFAP | WPG45 GYSP | WPG55 GRSP | | | | | | | | |
| Ex. 1 | 22.50 | 3.30 | 0.22 | 12.5 | 10.0 | 0.50 | 8.41 | 303.6 | 466.9 | 796.6 | 26.8 |
| Ex. 2 | 22.50 | 3.30 | 0.22 | 12.5 | 3.0 | 0.15 | 8.59 | 286.8 | 434.7 | 721.4 | 25.4 |
| | WPG75 PFAP | WPG45 GYSP | SIH RED No. 211P | | | | | | | | |
| Ex. 3 | 22.50 | 3.30 | 0.11 | 5.0 | 1.0 | 0.05 | 8.20 | 249.7 | 374.3 | 601.0 | 24.7 |
| Ex. 4 | 22.50 | 3.30 | 0.11 | 12.5 | 1.0 | 0.05 | 8.30 | 250.1 | 374.8 | 603.9 | 25.8 |
| Ex. 5 | 22.50 | 3.30 | 0.11 | 30.0 | 1.0 | 0.05 | 8.33 | 228.0 | 337.7 | 533.9 | 21.5 |
| Ex. 6 | 22.50 | 3.30 | 0.11 | 30.0 | 1.0 | 0.05 | 7.33 | 231.6 | 344.9 | 547.3 | 21.0 |
| Ex. 7 | 12.80 | 16.00 | 1.38 | 30.0 | 1.0 | 0.05 | 8.43 | 223.4 | 348.6 | 627.3 | 28.6 |
| Ex. 8 | 12.80 | 16.00 | 1.38 | 30.0 | 1.0 | 0.05 | 7.28 | 286.0 | 447.8 | 809.1 | 27.7 |
| | SIH TiO$_2$ R250 | SIH Yellow No. 602P | SIH RED No. 211P | | | | | | | | |
| Ex. 9 | 18.05 | 0.40 | 0.00 | 12.5 | 1.0 | 0.05 | 7.47 | 509.7 | 782.9 | 1326 | 19.9 |
| Ex.10 | 9.60 | 7.20 | 1.38 | 12.5 | 1.0 | 0.05 | 7.87 | 547.2 | 851.3 | 1436 | 25.6 |

Zeta Potential Measurements

Herein, "zeta potential" refers to the electrokinetic potential of the composition as measured by a NanoBrook Zeta-PALS Potential Analyzer from Brookhaven Instruments Corporation. It must be noted that the treatment compositions of the present invention may need to be diluted to achieve an accurate measurement of the Zeta potential of the particles contained within the treatment composition. Accordingly, the particulate concentration used to measure Zeta potential may or may not be different than the particulate concentration of the treatment composition. The Nano-Brook Zeta PALS utilizes phase analysis light scattering to determine the electrophoretic mobility of charged, colloidal suspensions. The samples were prepared as follows. Non-pigmented chasses were made with 0, 0.05%, and 0.15% Darvan 811D (Sodium Polyacrylate particulate suspending agent), respectively (1-3 and 18 in Table 2 below). Their pH was adjusted to 5, 7, or 9 using citric acid or AMP Ultra PC 2000. Using the individual raw slurries, additional formula were made using 1% active solid loading, 5% propylene glycol, 1.0% Symdiol, 1.5% PVP/VA, and varying levels of Darvan 811D (4-17 and 19-21 in Table 2 below). Zeta potential samples were prepared by diluting formula 4-17 and 19-21 to 0.1 g/ml into unpigmented chassis 1, 2, 3 or 18 that supports a pH of 5, 7, or 9. Zeta potential was measured on a NanoBrook ZetaPALS Potential Analyzer using the Smoluchowski zeta potential model with 5 runs and 10 cycles. After running a standard (BIZR3), the cells were loaded with 1 ml of zeta potential sample solutions. Zeta potential was measured as a function of pH and plotted below.

TABLE 2

| | Ingredient | Description | 1 % W/W | 2 % W/W | 3 % W/W | 4 % W/W | 5 % W/W | 6 % W/W | 7 % W/W | 8 % W/W | 9 % W/W | 10 % W/W |
|---|---|---|---|---|---|---|---|---|---|---|---|---|
| A | Water | Water | 92.5 | 91.5 | 89.5 | 91.15 | 90.25 | 90.66 | 91.5 | 90.15 | 89.25 | 89.66 |
| A | Propylene Glycol | Propylene Glycol | 5 | 5 | 5 | 5 | 5 | 5 | 5 | 5 | 5 | 5 |
| A | PVP/VA 735W | 50% VP/VA Copolymer in water | 1.5 | 1.5 | 1.5 | 1.5 | 1.5 | 1.5 | 1.5 | 1.5 | 1.5 | 1.5 |
| A | Symdiol | Hexanediol/Caprylyl Glycol | 1 | 1 | 1 | 1 | 1 | 1 | 1 | 1 | 1 | 1 |
| B | WPG75PFSP "Particle 1" | 75% TiO2 Slurry in Propylene Glycol/Water | 0 | 0 | 0 | 1.35 | 0 | 0 | 0 | 1.35 | 0 | 0 |
| B | WPG45GYSP "Particle 2" | 45% Iron Oxide Slurry Propylene Glycol/Water | 0 | 0 | 0 | 0 | 2.25 | 0 | 0 | 0 | 2.25 | 0 |
| B | WPG55GRSP "Particle 3" | 45% Iron Oxide Slurry Propylene Glycol/Water | 0 | 0 | 0 | 0 | 0 | 1.84 | 0 | 0 | 0 | 1.84 |
| B | SIH TiO2 R250 "Particle 4" | TiO2, Silica, and Aluminum Hydroxide | 0 | 0 | 0 | 0 | 0 | 0 | 0 | 0 | 0 | 0 |
| B | SIH Yellow No. 602P "Particle 5" | Iron Oxides C.I. 77492 and Silica | 0 | 0 | 0 | 0 | 0 | 0 | 0 | 0 | 0 | 0 |

TABLE 2-continued

| | Ingredient | Description | | | | | | | | | | |
|---|---|---|---|---|---|---|---|---|---|---|---|---|
| B | SIH RED No. 211P Particle 6" | Iron Oxides C.I. 77491 and Silica | 0 | 0 | 0 | 0 | 0 | 0 | 1 | 0 | 0 | 0 |
| C | Darvan 811D | 5% Sodium Polyacrylate in water | 0 | 1 | 3 | 0 | 0 | 0 | 0 | 1 | 1 | 1 |
| | | Total | 100 | 100 | 100 | 100 | 100 | 100 | 100 | 100 | 100 | 100 |

| | Ingredient | Description | 11 % W/W | 12 % W/W | 13 % W/W | 14 % W/W | 15 % W/W | 16 % W/W | 17 % W/W | 18 % W/W | 19 % W/W | 20 % W/W | 21 % W/W |
|---|---|---|---|---|---|---|---|---|---|---|---|---|---|
| A | Water | Water | 90.5 | 90.5 | 90.5 | 88.15 | 87.25 | 87.66 | 88.5 | 82.5 | 81.15 | 80.25 | 80.66 |
| A | Propylene Glycol | Propylene Glycol | 5 | 5 | 5 | 5 | 5 | 5 | 5 | 5 | 5 | 5 | 5 |
| A | PVP/VA 735W | 50% VP/VA Copolymer in water | 1.5 | 1.5 | 1.5 | 1.5 | 1.5 | 1.5 | 1.5 | 1.5 | 1.5 | 1.5 | 1.5 |
| A | Symdiol | Hexanediol/Caprylyl Glycol | 1 | 1 | 1 | 1 | 1 | 1 | 1 | 1 | 1 | 1 | 1 |
| B | WPG75PFSP "Particle 1" | 75% TiO2 Slurry in Propylene Glycol/Water | 0 | 0 | 0 | 1.35 | 0 | 0 | 0 | 0 | 1.35 | 0 | 0 |
| B | WPG45GYSP "Particle 2" | 45% Iron Oxide Slurry Propylene Glycol/Water | 0 | 0 | 0 | 0 | 2.25 | 0 | 0 | 0 | 0 | 2.25 | 0 |
| B | WPG55GRSP "Particle 3" | 45% Iron Oxide Slurry Propylene Glycol/Water | 0 | 0 | 0 | 0 | 0 | 1.84 | 0 | 0 | 0 | 0 | 1.84 |
| B | SIH TiO2 R250 "Particle 4" | TiO2, Silica, and Aluminum Hydroxide | 1 | 0 | 0 | 0 | 0 | 0 | 0 | 0 | 0 | 0 | 0 |
| B | SIH Yellow No. 602P "Particle 5" | Iron Oxides C.I. 77492 and Silica | 0 | 1 | 0 | 0 | 0 | 0 | 0 | 0 | 0 | 0 | 0 |
| B | SIH RED No. 211P Particle 6" | Iron Oxides C.I. 77491 and Silica | 0 | 0 | 1 | 0 | 0 | 0 | 1 | 0 | 0 | 0 | 0 |
| C | Darvan 811D | 5% Sodium Polyacrylate in water | 1 | 1 | 1 | 3 | 3 | 3 | 3 | 10 | 10 | 10 | 10 |
| | | Total | 100 | 100 | 100 | 100 | 100 | 100 | 100 | 100 | 100 | 100 | 100 |

To make the treatment compositions in Table 2, first combine ingredients of Phase A into the main container. Mill on low speed until mixture is homogenous. If adding Phase B, increase milling to high speed and add the ingredients of Phase B into the main container. Mill at a high speed for 15 minutes until mixture is homogenous. Add ingredient of Phase C to the main container. Mill for an additional 2-3 minutes to ensure homogeneity then pour into a container, label, and store at ambient conditions.

Below are the results of the Zeta potential measurements for the samples in Table 2. The results are grouped by particle, with the corresponding column number given for each data point in the raw data.

TABLE 3

| | Column | | | | | | | |
|---|---|---|---|---|---|---|---|---|
| | 4 | | 8 | | 14 | | 19 | |
| pH | mV | STDEV | mV | STDEV | mV | STDEV | mV | STDEV |
| 5 | −19.27 | 1.22 | −35.21 | 1.59 | −39.70 | 1.01 | −33.63 | 1.14 |
| 7 | −37.57 | 1.78 | −52.70 | 1.60 | −49.15 | 1.84 | −40.53 | 2.86 |
| 9 | −30.49 | 0.67 | −55.82 | 0.88 | −52.20 | 1.80 | −41.04 | 3.79 |

TABLE 4

| | Column | | | | | | | |
|---|---|---|---|---|---|---|---|---|
| | 5 | | 9 | | 15 | | 20 | |
| pH | mV | STDEV | mV | STDEV | mV | STDEV | mV | STDEV |
| 5 | −17.47 | 1.08 | −25.03 | 0.81 | −35.29 | 1.30 | −24.36 | 1.54 |
| 7 | −33.99 | 0.90 | −48.37 | 1.54 | −51.86 | 0.88 | −32.61 | 2.43 |
| 9 | −24.84 | 1.37 | −52.76 | 0.93 | −52.49 | 1.32 | −30.81 | 2.26 |

TABLE 5

| | Column | | | | | | | |
|---|---|---|---|---|---|---|---|---|
| | 6 | | 10 | | 16 | | 21 | |
| pH | mV | STDEV | mV | STDEV | mV | STDEV | mV | STDEV |
| 5 | −12.56 | 0.48 | −13.60 | 1.00 | −19.30 | 1.28 | −25.40 | 2.99 |
| 7 | −27.59 | 2.97 | −45.58 | 1.31 | −45.26 | 1.60 | −20.97 | 1.91 |
| 9 | −21.97 | 0.69 | −42.48 | 1.94 | −45.48 | 0.68 | −36.20 | 2.03 |

TABLE 6

| | Column | | | | | |
|---|---|---|---|---|---|---|
| | 7 | | 13 | | 17 | |
| pH | mV | STDEV | mV | STDEV | mV | STDEV |
| 5 | −7.38 | 0.42 | −9.39 | 0.90 | −8.91 | 1.40 |
| 7 | −2.97 | 1.41 | −15.37 | 0.58 | −11.46 | 1.53 |
| 9 | −4.50 | 1.48 | −21.71 | 1.37 | −15.87 | 0.93 |

TABLE 7

| | Column | | | | | |
|---|---|---|---|---|---|---|
| | 11 | | 12 | | 13 | |
| pH | mV | STDEV | mV | STDEV | mV | STDEV |
| 5 | −7.79 | 0.99 | −10.74 | 0.66 | −9.39 | 0.90 |
| 7 | −11.42 | 0.71 | −16.74 | 0.65 | −15.37 | 0.58 |
| 9 | −19.00 | 1.51 | −30.79 | 1.05 | −21.71 | 1.37 |

Tables 3-7 and the raw data graphed in these Tables, as shown in corresponding FIGS. 13-17, demonstrate a variety of conditions from which the present invention is drawn. Specifically, the treatment compositions of the present invention preferably have a pH that falls within the range of 5-10. Further, these compositions have a Zeta potential of negative 20 or less, or greater than positive 20, preferably, negative 30 or less, or greater than 30. It is important to note that zero on the zeta potential graph indicates no charge on the particles. Thus, negative 20 and positive 20 represent particles with either a negative charge or a positive charge of 20. Both positive and negative charges are preferred over zero charge for the particles of the present invention. To be clear, it is desired to have the particles charged, it is not important if the overall zeta potential is positive or negative.

A particle size distribution D50 within the range of about 200 ηm to about 500 ηm, and a D90 of less than about 1 μm is preferred. As described above, these preferred ranges were developed based on the rate at which particles settle out of the treatment composition, and the ease with which these particles could be moved back into solution after settling.

PSD Measurement

Herein, "PSD" refers to the particle size distribution of the composition as measured by a Horiba LA-950V2. The Horiba LA-950V2 Laser Scattering Particle Size Distribution Analyzer uses the principles of Mie and Fraunhofer scattering theories for calculating the size and distribution of particles suspended in a liquid. The range of particle size measured is from 0.01 to 3000 μm on the LA950V2. Results are normally displayed on a volume basis. The application of this method to pigments has been developed using a flow cell procedure. Samples were prepared by vortexing for 30 seconds with a Vortex Genie 2 to ensure there is no residue in the bottom of the sample vial. 200 ml of DI water was added into the instrument and analyzed as a blank sample. A disposable micro pipet was used to dispense enough sample into the DI water in the instrument until the Transmittance was reduced from 100 down to 90+/−2%, approximately 250 μL. Results are reported as D10, D50, and D90 in Table 2.

TREATMENT APPARATUSES

One example of how to use the treatment compositions of the present invention is in a device or apparatus to detect and modify tonal variations on human skin. To better understand how the apparatuses of the present invention work, and why they are so beneficial to the consumer, it is best to understand first what the device does. The present methods, in their simplest form, are directed to analyzing and treating tonal imperfections on human skin that comprises the steps of taking at least one background image of at least 10 μm$^2$ of skin and then calculating the average background L value of the image on a grey scale. Further, from the same image, a localized L value is calculated for individual pixels or a group of pixels. The local L value is then compared to the background L value to identify skin deviations. A skin deviation is an area of skin where the absolute value of the difference between a local L value and the background L, (this difference being defined as "$\Delta L_M$" or the measured $\Delta L$, "Δ" is commonly defined as the symbol for a difference between two values) is greater than a predetermined $\Delta L_S$. The background L can be preset, or calculated by a variety of methods described below. The skin deviations are then treated with a treatment composition having a predetermined or variable contrast ratio.

The background L can be calculated anywhere within the image. The image is taken where the nozzles will fire the treatment composition. The background L can be the arithmetic average, median, or mean of a plurality of local Ls, which means the calculation can include all of the local Ls in the image, or a subset thereof.

Likewise, there are provided apparatuses for treating human skin. The apparatus has an applicator head that includes multiple applicator nozzles and a reservoir for containing a treatment composition, which can be a skin treatment composition. There is further provided a sensor and a CPU. The sensor takes an image of at least 10 μm$^2$ of skin and the CPU analyzes the image to calculate the average background L value. The sensor output is also used to calculate the localized L value of individual pixels or groups of pixels of skin. The CPU then compares the local L value to the background L value to identify skin deviations where the difference between the two L values is greater than a predetermined value.

Exemplary treatment compositions for use with the present system include cosmetics, polymerics, aqueous, non-aqueous, particle loaded, optical modifier, fillers, optical matchers, skin actives, nail actives, hair actives, oral care actives, anti-inflammatory, antibacterial, surfactant or surfactant containing active, quantum dots and combinations thereof. Exemplary surfaces and substrates for the application of the treatment composition by the present deposition system include keratinous surfaces, woven surfaces, nonwoven surfaces, porous surfaces, non-porous surfaces, wood, teeth, tongue, metallic, tile, fabric, and combinations thereof The central processing unit ("CPU") of the device can be any of a variety of commercially available devices. In its simplest form, the CPU is a single programmable chip like those found in consumer electronic devices such as a lap top computer, a cell phone, an electric razor and the like. Those skilled in the art will know of a variety of commercially available chips and other processors suitable for use with this invention. CPU may include Application Specific Integrated Circuit (ASIC), controller, Field Programmable Gate Array (FPGA), integrated circuit, microcontroller, microprocessor, processor, and the like. The CPU may also include memory functionality, either internal to the CPU as cache memory, for example Random Access Memory (RAM), Static Random Access Memory (SRAM) and the like or external to the CPU for example as Dynamic Random-Access Memory (DRAM), Read Only Memory (ROM), Static RAM, Flash Memory (e.g., Compact Flash or SmartMedia cards), disk drives, Solid State Disk Drives (SSD) or even Internet Cloud storage. While it is anticipated that a remote CPU, either tethered to the device, or which communicates wirelessly, can be used to accomplish the methods of the present invention, a local CPU within the device is exemplified herein. Size and speed of the CPU is an important consideration of the design parameters, but cost and other considerations will be considered by the device designers.

The predetermined $\Delta L_S$ is the absolute value of the difference between the local L and the background L. This value, $\Delta L_S$, can be defined in absolute numbers or as a percentage. The sensor is for example a camera that takes black and white or color images, a spectrophotometer or similar devices that are sensitive to electromagnetic wavelengths. The images are taken, or converted to a standard grey scale that is known to the art. It is understood that any numerical scale that measures lightness to darkness can be considered a "grey scale". Moreover, as used herein, "grey scale" is intended to be a linear scale, or one band, or one visual attribute. For example, one "grey scale" visual attribute could be single wavelength or a narrow wavelength to define a specific visual color. Another example of one "grey scale" visual attribute could be a mix of wavelength numerical values averaged for each pixel making up the image, such as a true black, grey or white image from an RGB mixture.

It will also be understood to those skilled in the art that the background L value should not be too close to the ends of this scale. For example, if the grey scale is 0-100, with 0 being pure black and 100 being pure white, a background in the 0-10 range, or in the 90-100 range may be too light or too dark to show meaningful differences. Accordingly, one can adjust the background lighting, or the gain on the camera taking the image, to move the background L closer to the middle of the scale. In this example, a background L of 50 would be ideal, with a background L in the range of 10-90 preferred, 20-80 even more preferred.

The most common grey scale is 0-255 (no units) other examples include 0-1024 and 0-4096. In this example it would be desirable to use camera and lighting settings that provide a background L value between 60 and 210. Using the 0-255 gray scale the $\Delta L_S$ is preferably at least 0.5, more preferably at least 1 and even more preferably at least 1.5, to initiate treatment of the skin. Likewise, $\Delta L_S$ can be measured as a percentage, for example, a numerical $\Delta L_S$ of 2.6 is approximately equal to 1.0% of a 255 grey scale. Thus $\Delta L_S$ may be plus or minus 0.25%, preferably plus or minus 0.5% even more preferably plus or minus 0.75%, of the grayscale.

The skin treatment compositions used to hide, or more appropriately, to camouflage a skin deviation are described and exemplified in greater detail below. One important characteristic of the skin treatment compositions of the present invention is the contrast ratio. The contrast ratio of the treatment composition when treating the skin is at least 0.1. The skin lightness and treatment composition lightness can be measured by a calibrated spectrophotometer using known methods. In the case of using a calibrated spectrophotometer, the average L value of human skin usually spans the range of about 25 to 75. In this case the corresponding treatment composition has a lightness value of at least 2 units greater, preferably at least 3 units greater, and even more preferably at least 5 units greater than the average skin lightness value of the consumer.

Images are taken in sequence or preferably continuously. A camera that takes a minimum of 4 frames per second is preferred. Higher speed cameras (greater than 4 frames per second) are desired as well, for example greater than 200 frames per second. All images are either taken in a grey scale or converted to a grey scale, the grey scale can have any range, for example, 0-255, no units. This corresponds approximately to a refresh rate of 0.2 seconds or faster.

There is no technical difference between an image used for background L values and those used for local L values, the difference is in the analysis of the image. Hence, the images are continually sent to the CPU, that is, the processing unit, to calculate the L values, and $\Delta L_M$ values. By "sent" it is understood, that preferably at least 4 bits of data per pixel are transferred for each image, and preferably, this 4 bit (or more) packet of data is used in the calculation of each local L value. It is understood, that the background L can be calculated once in a treatment period and that value reused throughout the treatment period. Or it can be continually recalculated as long as the treatment process goes on. Moreover, there can be pre-programmed triggers to initiate a recalculation of the background L. Also, the background L may be retrieved from the CPU memory to be used for the current background L. For example, if an extended period of time elapses and no skin deviations are found, or if skin deviations are being found too frequently, a new background L might automatically be calculated. Likewise, $\Delta L_S$ can be a set value that remains constant throughout the treatment cycle or it too can vary. $\Delta L_S$ can be reset during the treatment cycle for any of a variety of reasons. If too many nozzles are firing too frequently, the $\Delta L_S$ can be adjusted to lower the intensity of the nozzle firing. Similarly, if the nozzles are firing too infrequently, $\Delta L_S$ can be adjusted in the opposite direction to increase the sensitivity of skin deviation detection. Those skilled in the art will appreciate that modifying $\Delta L_S$ during treatment is a matter of programming the CPU to a desired algorithm.

When the $\Delta L_M$ exceeds the predetermined value, the skin deviation is treated with the treatment composition. Treatment requires firing one or more of the nozzles which dispense the treatment composition onto the skin in the area of the skin deviation. Preferably the treatment composition is applied to the skin deviations in a discontinuous deposition pattern of discrete droplets between about 1 μm to about 100 μm in size. It is also preferred that no more than 85% of the skin deviation is covered by the treatment composition. More specifically, the treatment composition is applied via a array of nozzles and the local L is calculated along the length of, and in the firing range of, the array of nozzles. The "array" can be a linear configuration, multiple rows, off-set, sine wave, curved, circular, or saw tooth arrangements of nozzles. Those skilled in the printing arts will appreciate the various configurations of nozzle arrays that are possible for use in the methods and apparatuses disclosed herein. The "firing range" of a nozzle will vary based on its size, type, the speed the device is moving, distance from the target, and other parameters. Examples of various types of nozzles suitable for use in the present devices are given below. But in general, "near the nozzle" as used herein is meant to mean the image taken to calculate a local L value is close to the area of skin where the treatment composition is deposited by the nozzle (the firing range, or landing zone of the nozzle). Without intending to limit the invention, near the nozzle means the image should be taken within a radius of about 2 cm, preferably about 1 cm and even more preferably, about 0.7 cm from the center of the nozzle.

An individual nozzle may be fired to deposit the treatment composition, or multiple nozzles fired at the same time. The number of nozzles fired along the linear array of nozzles can be adjusted based on the size of the $\Delta L_M$ and the size of the skin deviation. Furthermore the frequency of nozzle firing can be adjusted based on the $\Delta L_M$, with more droplets being fired in succession in response to larger $\Delta L_M$ values.

Firing intensity curves can be programmed into the CPU to adjust the firing rate of nozzles. For example, if $\Delta L_M$ is equal to or slightly greater than $\Delta L_S$, then the adjacent nozzle is fired 1 time. If $\Delta L_M$ increases to $2*\Delta L_S$, then the adjacent nozzle is fired 25 times. If the $\Delta L_M$ is $3*\Delta L_S$, then the adjacent nozzle is fired 100 times. This non-limiting example is intended to show how the size of the $\Delta L_M$ with respect to the $\Delta L_S$ can determine the amount, and hence, the intensity of the firing of the nozzles adjacent the skin deviation. Those skilled in the art will appreciate that plotting a firing intensity curve using 2, 3 or more data points, and then programming that firing intensity curve into the CPU are known techniques.

The methods and apparatuses used by the present invention can be briefly summarized as follows. Referring now to FIG. 1, where analytical window 10 is an area that comprises a sample of skin 12 and nozzle array 20. Nozzle array 20 contains individual nozzles that are off or not firing 24, and individual nozzles that are firing 22. Skin deviations 30 and 31 are shown underneath nozzle array sections 32 and 33. Background L is calculated on and around skin area 12, skin area 14 is where local $L_1$ is measured and skin area 16 is where local $L_2$ is measured. Skin area 14 is under nozzle array 20 but not within a skin deviation. Thus, the absolute value of local $L_1$—background L ($\Delta L_{1M}$) is less than the preset threshold to initiate nozzle firing. The $\Delta L_S$ threshold required to initiate nozzle firing is a variable and is dependent on the scale used. For example, in a case where the 0-255 gray scale is utilized then the $\Delta L_S$ threshold required to initiate nozzle firing would commonly be a value of 2 or greater. Thus in the example shown in FIG. 1 the value of $\Delta L_{1M}$ is less than 2. Likewise, skin area 16 is within skin deviation 30, and the absolute value of local $L_2$—background L ($\Delta L_{2M}$) is greater than about 2. Thus the nozzles around skin areas 24 and 14 are generally off, and the nozzles around skin area 16 are generally firing. To insure the nozzles do not clog with particles or dried treatment composition, any nozzle can be fired at any time simply to keep it clean and "healthy". And as discussed above, the number of nozzles directly over a skin deviation that are fired in response to the skin deviation can be adjusted based on the size of $\Delta L_S$, the size (e.g., surface area) of the skin deviation or other parameters devised by those skilled in the art.

Treatment times will vary based on the size of the treatment area and the precision and amount of the treatment. For example, a woman may wish to simply touch up a few small areas on her face before going to grocery store. This treatment might take a few minutes. Alternatively, a young bride might wear her wedding dress to a salon where a salon professional meticulously treats all exposed areas of skin prior to the wedding and the taking of her wedding pictures. This full body treatment might take hours. Accordingly, the consumer will have tremendous control over the amount of time they choose to use the present device.

Figure 2:
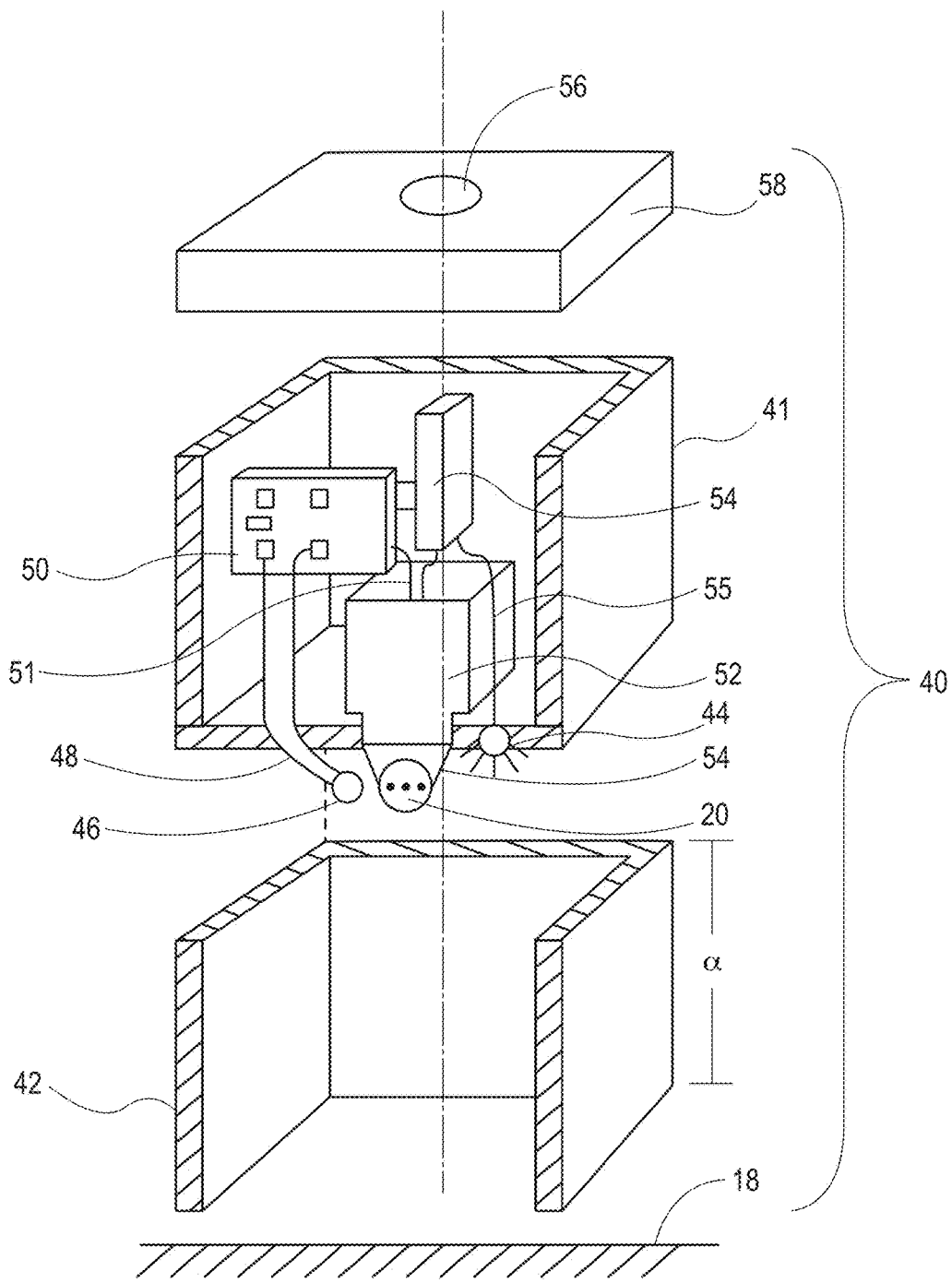
FIG. 2 is a hand held apparatus according to the present invention.

Referring now to FIG. 2, which shows a handheld apparatus 40 according to the present invention. The term "line" as used herein means a line, or method of communication between two elements. This line of communication, for example, image capture line 48, can be a physical connection such as a hard wire or it can be a wireless communication as described herein.

Apparatus 40 is directly above skin 18, separated by physical spacer 42. Physical spacer 42 has a set, predetermined height α such that when it contacts skin 18, the mechanical and electrical elements above the skin are all at a known distance from the skin. The mechanical and electrical elements are associated with apparatus 40 and include, but may not be limited to, light 44, image capture device 46, nozzle array 20 which is embedded on cartridge die 54 which is attached to printer cartridge 52. All of these elements are enclosed within optional apparatus housing 41. Light 44 illuminates the area skin 18 within spacer 42 such that the image capture device 46 has relatively constant illumination. Background lighting will affect the image capture as portions of spacer 42 lift off of skin 18 and allow background light in and the illumination from light 44 to escape, but small deviations in illumination can be corrected for provided light 44 provides a relatively constant background illumination. Light 44 can be a light emitting diode (LED), incandescent light, neon based or any other commercially available source of illumination. Light 44 can have constant illumination or adjustable illumination. For example, an adjustable light source might be useful if the background illumination is excessively bright or dark.

Image capture device 46 can be any of a variety of commercially available devices such as a simple camera or a digital cmos camera chip. Image capture device 46 takes a picture of skin 18 and sends it to processor 50 via image capture line 48 for analysis. Processor 50 is generally referred to as a central processing unit, or CPU, which may comprise a simple circuit board, a more complex computer, or the like and may include memory functionality. Those skilled in the art will appreciate that a CPU can be any of wide variety of commercially available programmable devices. As described above, the image may be analyzed for local L values, background L values or both. Grey scale conversion occurs within the analytical processing capabilities of processor 50. The comparison of background L to local L to determine the $\Delta L_M$ occurs within processor 50, which can be a commercially available programmable chip, or other commercially available processing units.

Further provided is optional external CPU 43. External CPU 43 may be in communication with any or all of the electronic components of the apparatus described herein. By way of example, external CPU 43 can communicate with CPU processor 50 via external CPU communication line 45 and communicate with sensor 20 via sensor external communication line 47. Lines 47 and 45 can be physical communication lines or, more preferably, they are wireless communication lines.

The results of the image analysis, when compared to criteria pre-programmed into the processor, may result in a desired treatment of the skin. In such a case, for example when the calculate $\Delta L_M$ exceeds the pre-determined $\Delta L_S$, a signal is sent from processor 50 to cartridge 52, via cartridge line 51, to fire one or more of the nozzles in nozzle array 20. Power for cartridge 52, light 44, image capture device 46, processor 50, and other mechanical and electrical elements that might be present is supplied by power element 54 via multiple power lines 55. Power element 54 can be turned off and on, which in turn turns apparatus 40 off and on, via power switch 56 which can be located anywhere on apparatus 40 but is shown here on apparatus cover 58. Power element 54 may include energy storage functionality via a rechargeable battery, a double-layer capacitor, a supercapacitor or a hybrid battery-capacitor system.

Figure 3:
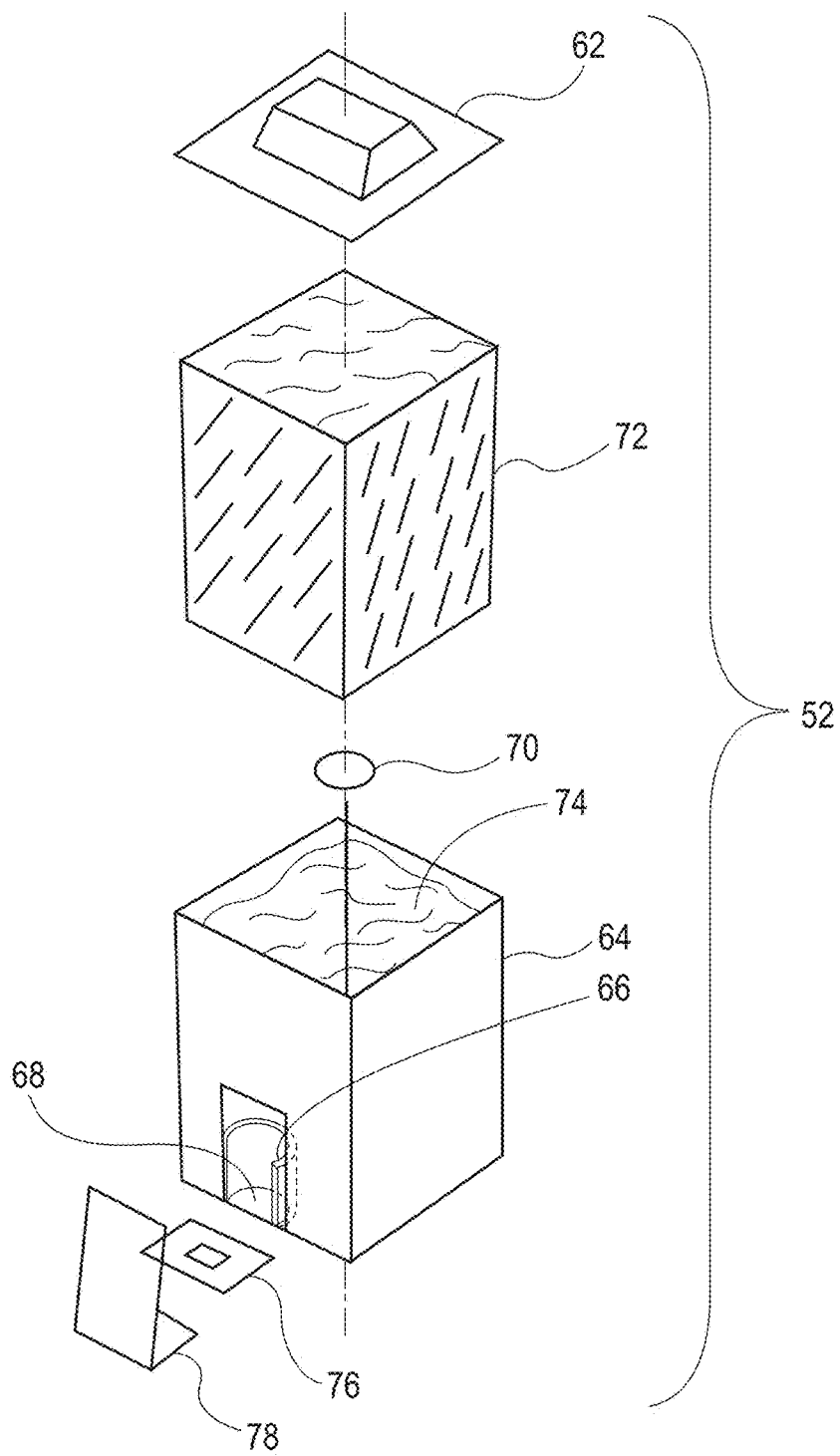
FIG. 3 is an ink jet cartridge according to the present invention.

Turning now to FIG. 3 which is an exploded view of the cartridge 52 comprising cartridge cap 62 and cartridge body 64. Body 64 includes standpipe 66 which is typically enclosed within body 66 and defines nozzle outlet 68. Optional filter 70 helps keep excessively large particles, and other debris out of the nozzle array 76. Filter 70 and nozzle array 76 are on opposite sides of nozzle outlet 68. Treatment composition 74 partially fills cartridge body 64. Foam core 72 fills cartridge 64 and helps to regulate back pressure of the treatment composition 74. While a foam core cartridge is used to describe and exemplify back pressure can be regulated via bladders (not shown) and other methods known to the art, the foam core shown here is just one example of how to help regulate flow of the treatment composition 74 to standpipe 66 through filter 70 and into nozzle array 76. Connector 78 provides the electrical power and signal to nozzle array 76. Connector 76 may be in wireless communication with the CPU processor 50, external CPU 43, sensor 20 or any other electronic component of apparatus 40 and external apparatus associated therewith.

Treatment composition 74 within cartridge body 64 may comprise particles and the treatment compositions preferably have a particle settling rate of less than 0.06 mm per day at 25° C. and 1 atm pressure. The treatment composition may further have an elastic modulus between about 0.1 Pa to about 1000 Pa at 25C and 1000 Hz. Preferably, the particles in the treatment composition have a refractive index of between about 1.1 and about 5.0.

Figure 7:
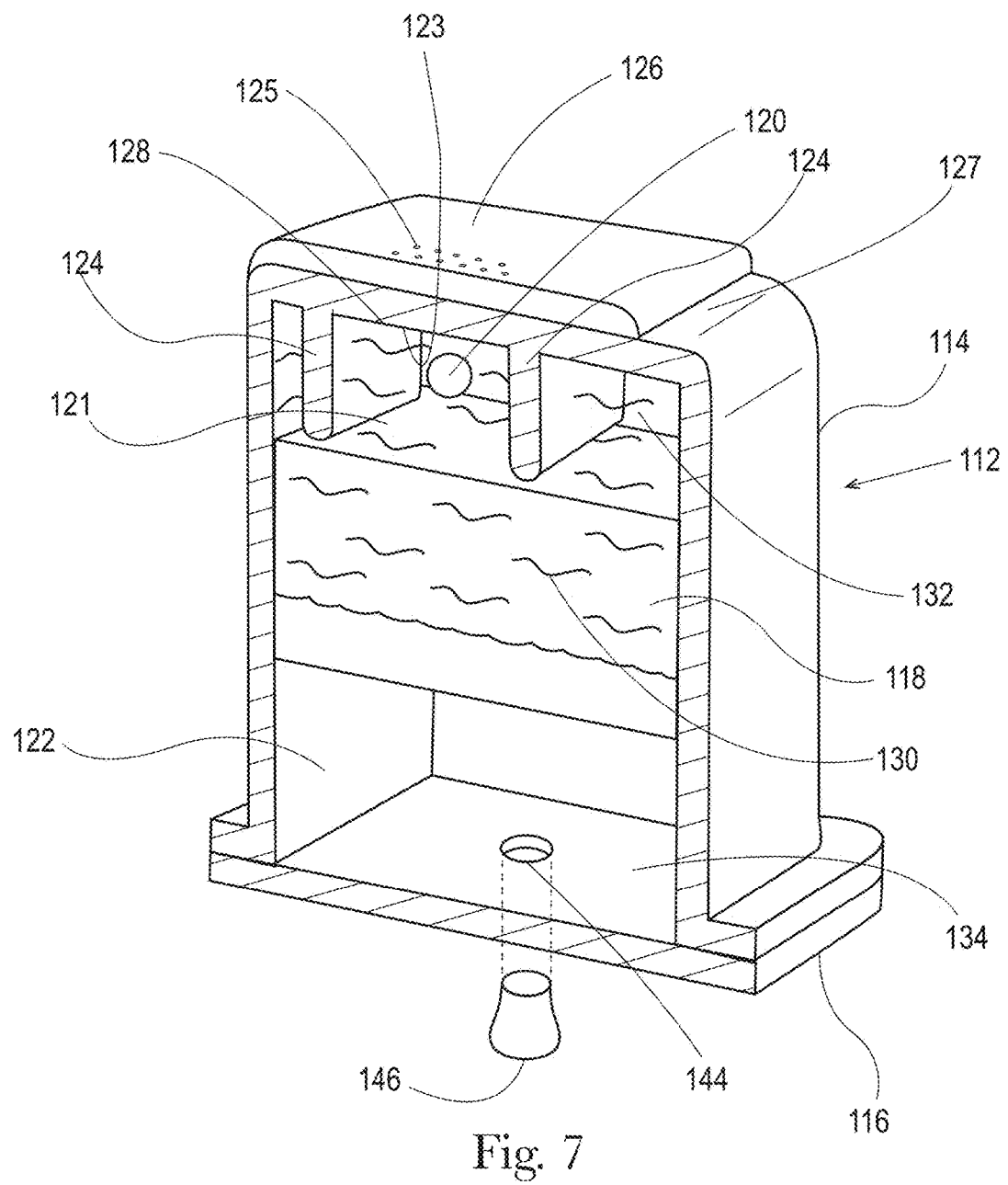
FIG. 7 is a cartridge assembly according to the present invention showing a possible placement position for a treatment composition dispersing device.

Turning now to FIG. 7, which shows cartridge assembly 112 that has a cartridge body 114 and a cartridge base 116, which collectively define cartridge reservoir 122. The size, shape and configuration of the cartridge assembly will vary based on the device in which it will be used. Cartridge assembly 112 is generally a rectangular box, but many other configurations will be known to those skilled in the art and are all considered within the scope of the present invention. Die 126 is shown on one end of cartridge assembly 112. Die 126 contains nozzles 125 and wiring (not shown) which are used to deposit treatment composition 130 from the cartridge reservoir 122 to the surface being treated (not shown). While die 126 can be positioned anywhere on the exterior of the cartridge assembly 112, it is preferably adjacent standpipe 121.

Standpipe 121 is within cartridge reservoir 122 and is defined by standpipe wall 124 and standpipe base 123. The volume within standpipe 121 is standpipe reservoir 128. As discussed earlier, standpipe 121 and die 126 are adjacent one another and share a common wall. Accordingly, standpipe wall 124 comprises a portion of die wall 127 of cartridge body 114. The die/standpipe combination can be placed on any of the walls of cartridge body 114 or even cartridge base 116. The volumetric ratio of standpipe reservoir 128 to cartridge reservoir 122 is discussed in greater detail with respect to FIGS. 9-12.

Figure 8:
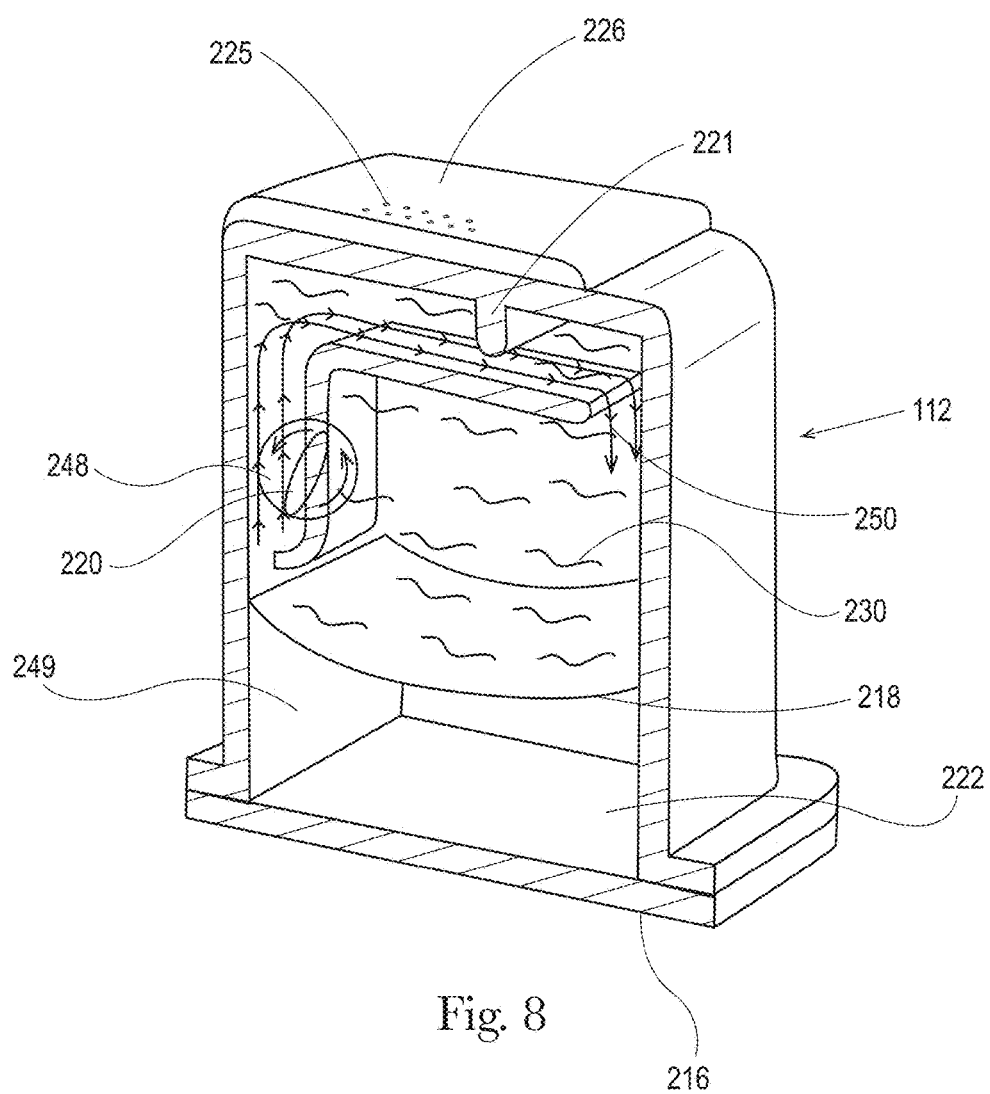
FIG. 8 is a cartridge assembly according to the present invention showing an alternate form of a treatment composition pressure element and treatment composition dispersing device.
Figure 13:
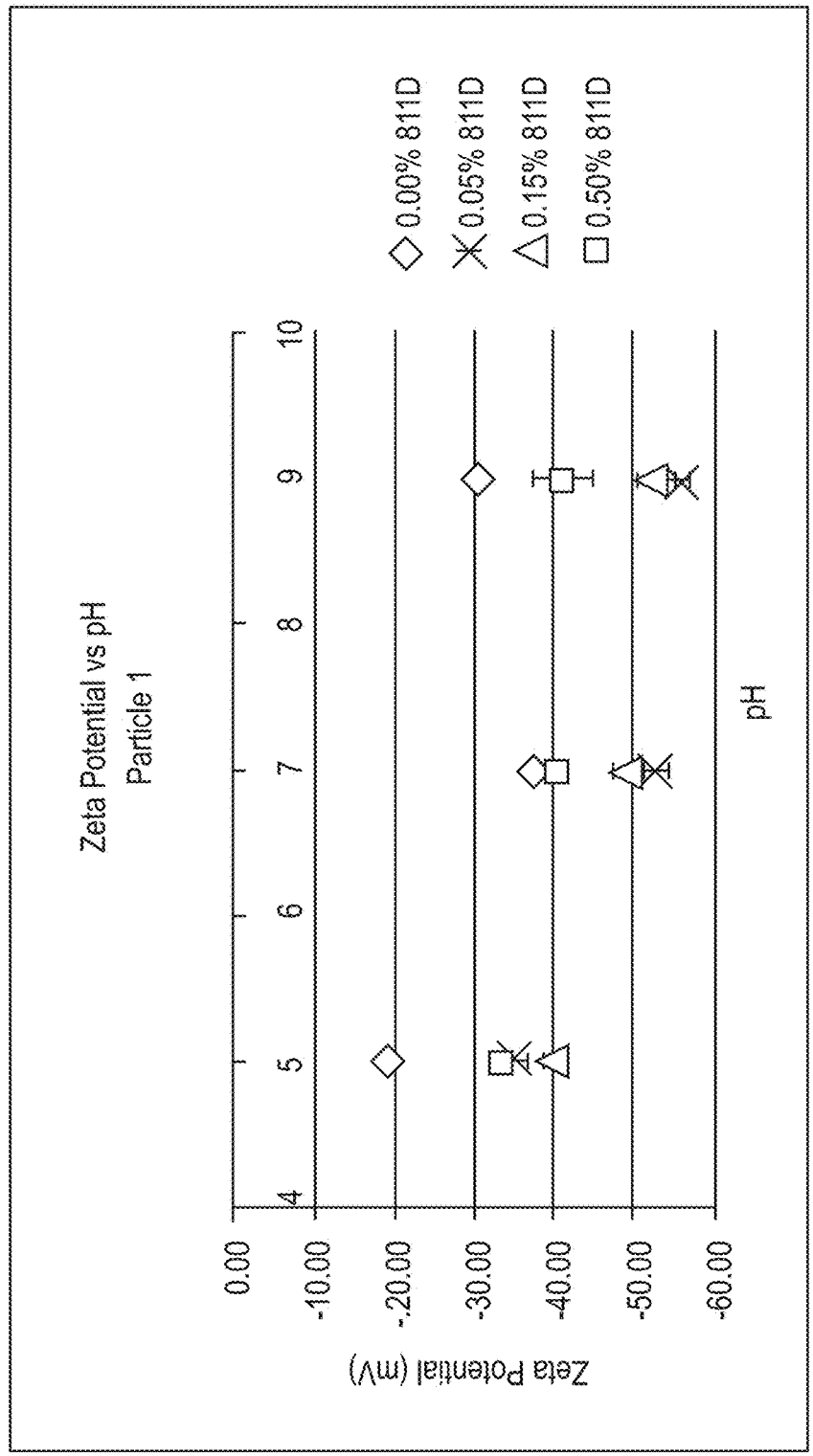
FIG. 13 is a graphical representation of the data in Table 3 for the Zeta Potential v. pH of Particle 1.
Figure 14:
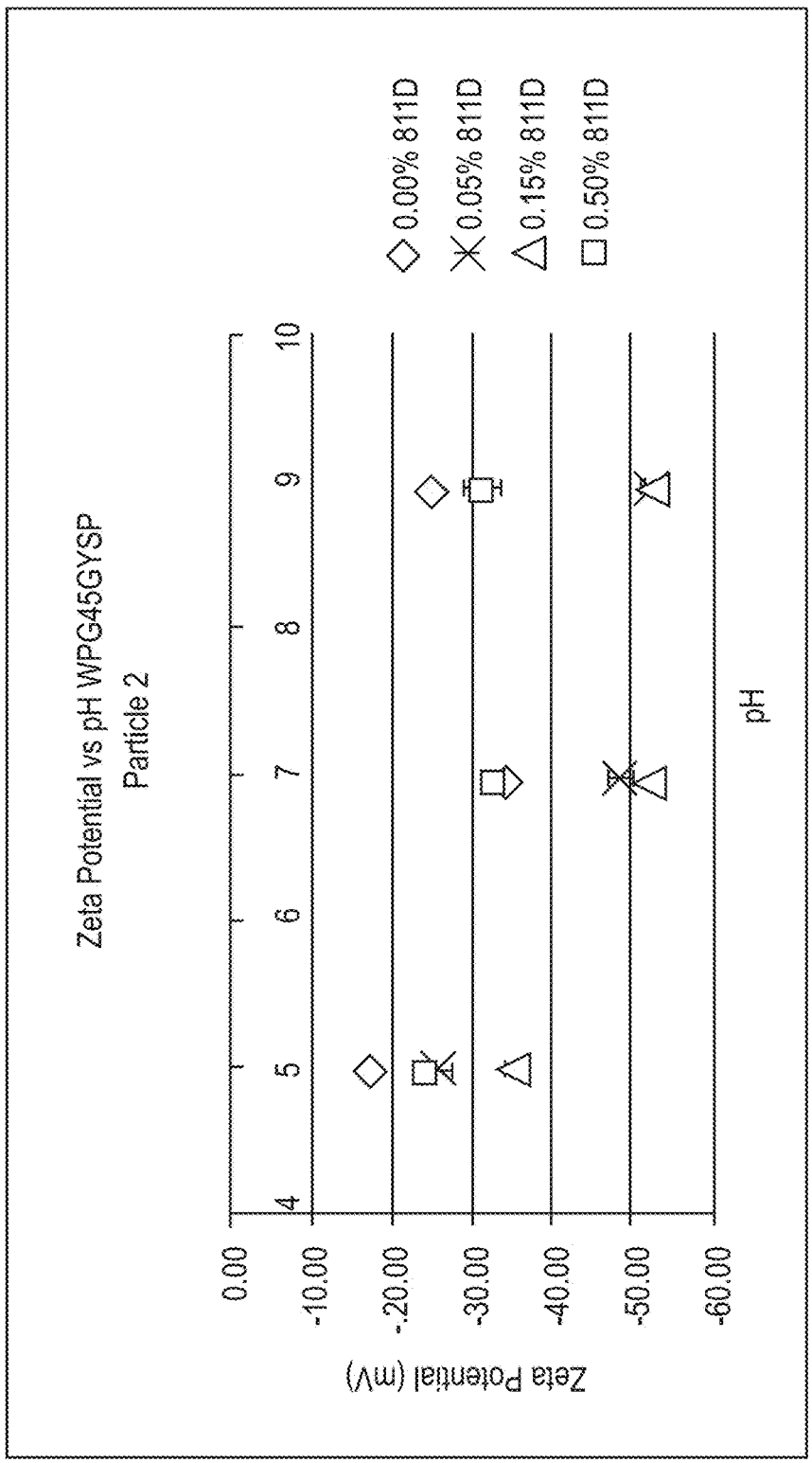
FIG. 14 is a graphical representation of the data in Table 4 for the Zeta Potential v. pH of Particle 2.
Figure 15:
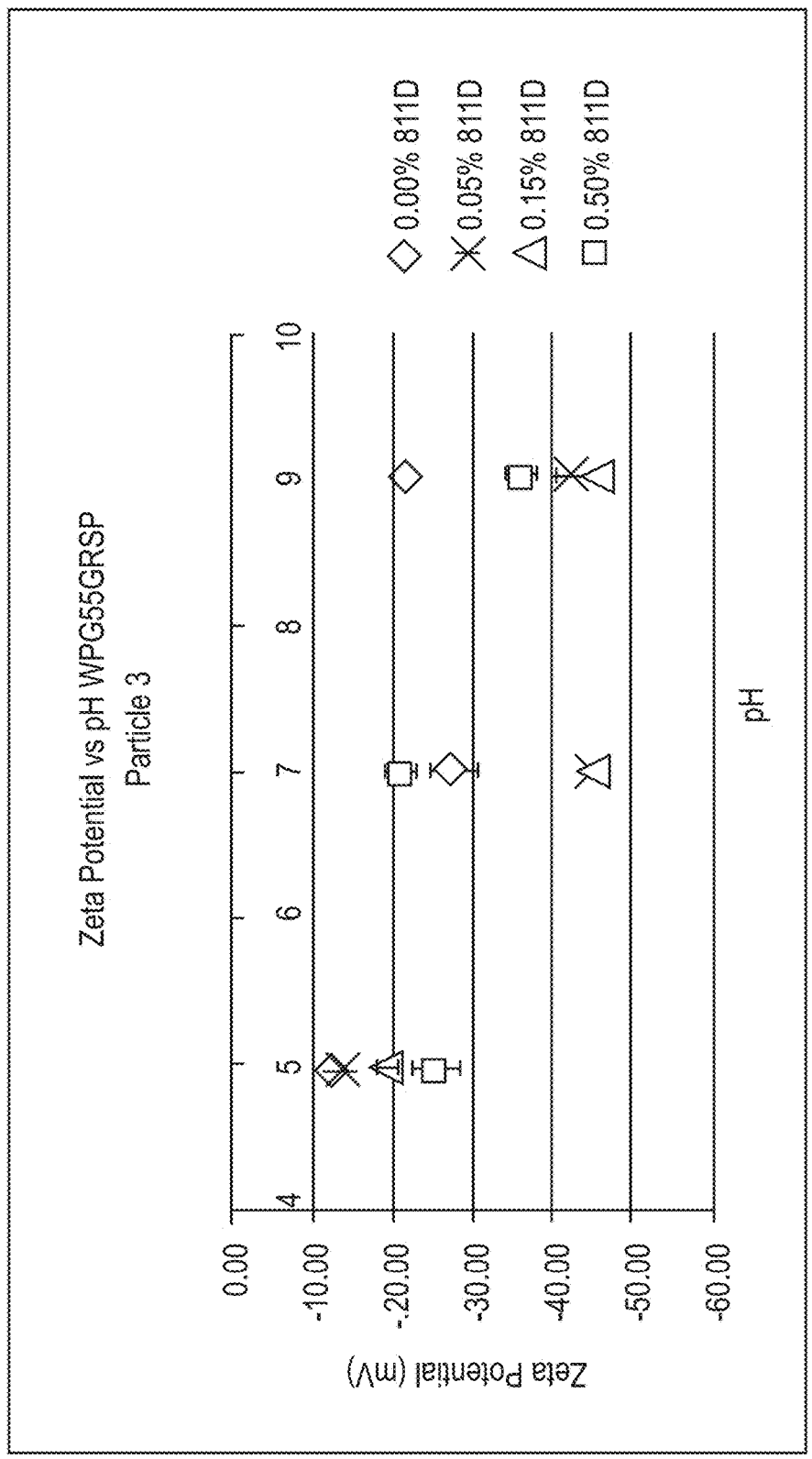
FIG. 15 is a graphical representation of the data in Table 5 for the Zeta Potential v. pH of Particle 3.
Figure 16:
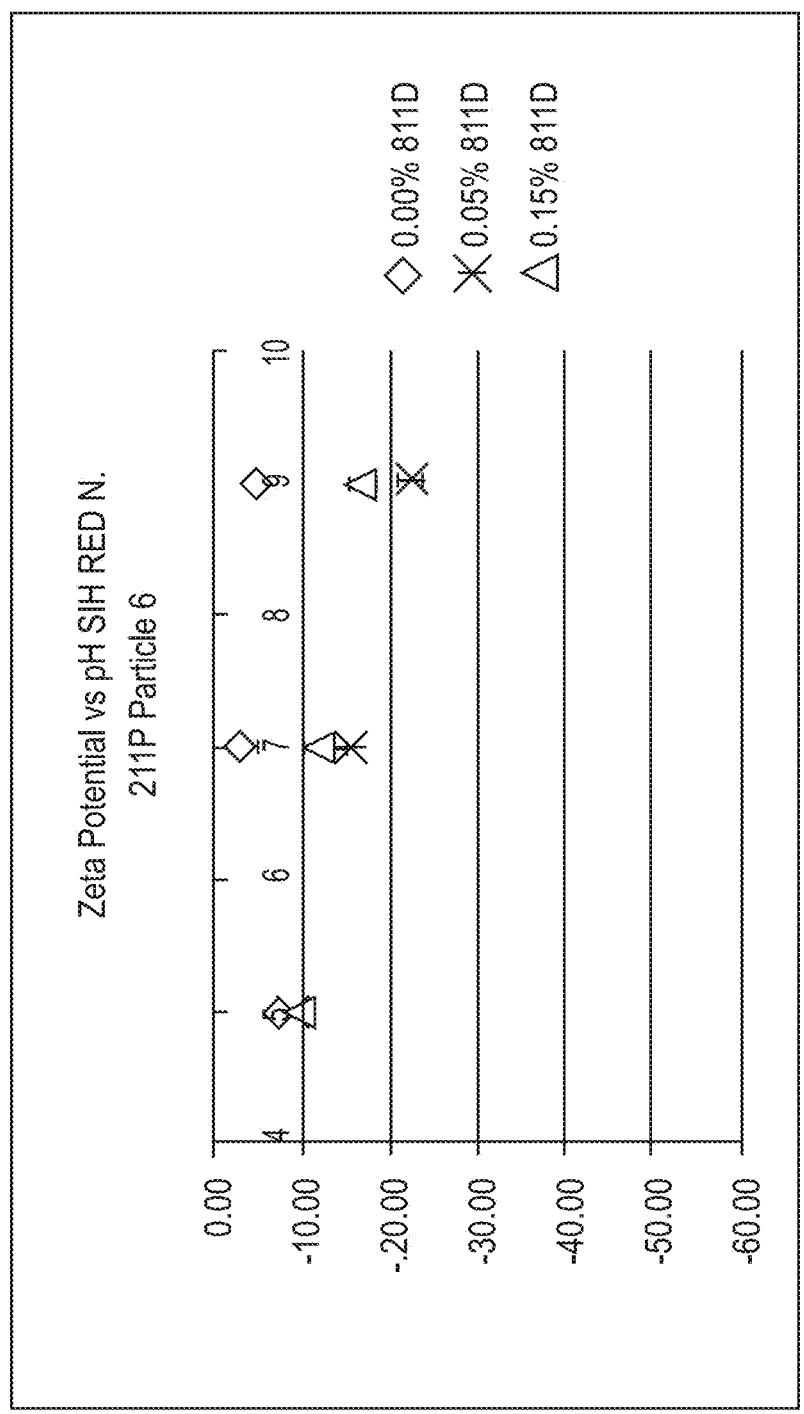
FIG. 16 is a graphical representation of the data in Table 6 for the Zeta Potential v. pH of Particle 6; and, FIG. 17 is a graphical representation of the data in Table 7 for the Zeta Potential v. pH of the Pigments.
Figure 17:
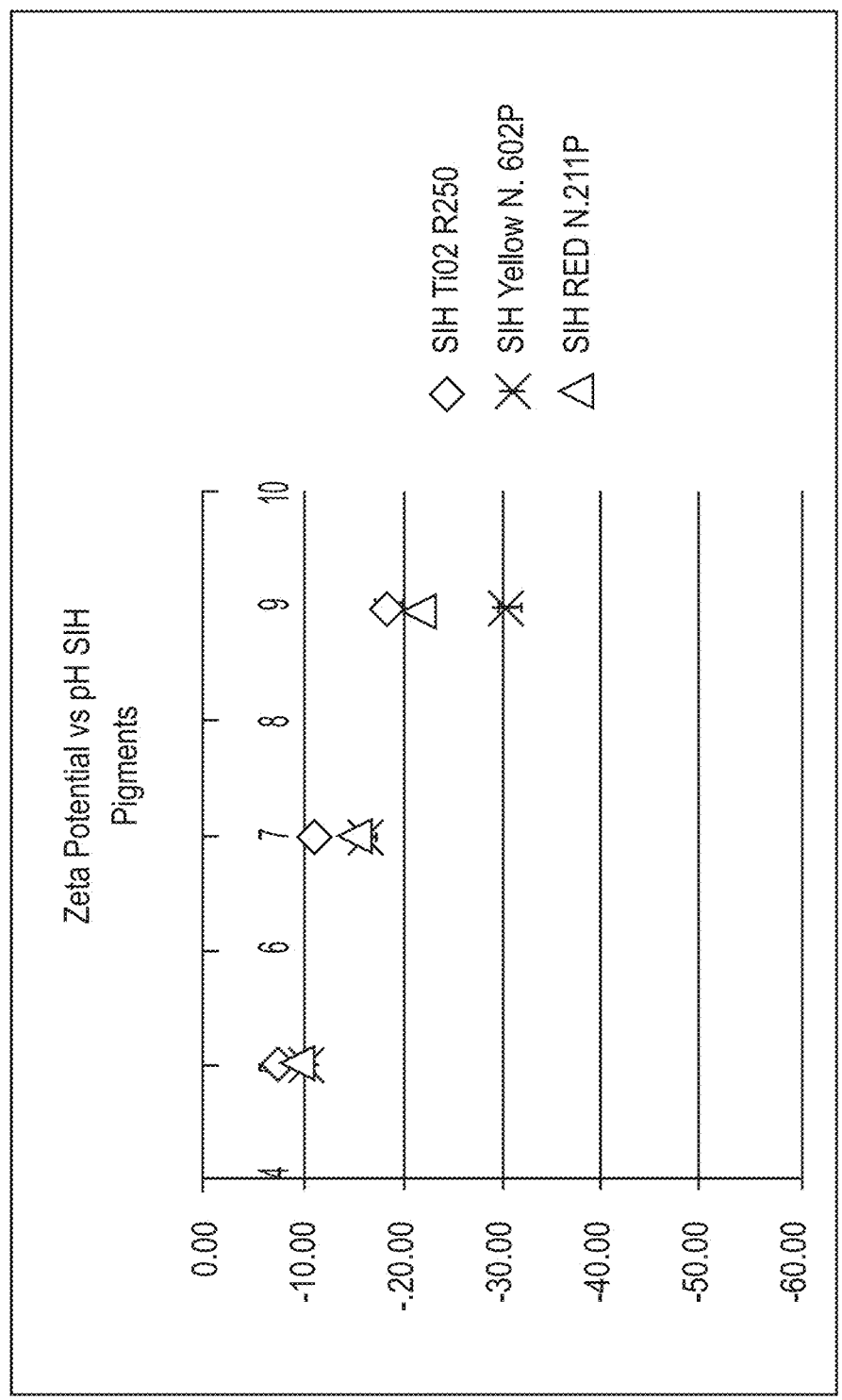

A treatment composition pressure element 118 is shown in FIG. 7 as a block of foam that fills a portion of cartridge reservoir 122. FIG. 8 shows treatment composition pressure element 218 in cartridge reservoir 222 of cartridge assembly 212. Treatment composition 130 (FIG. 7) fills cartridge reservoir 122 and flows through treatment composition pressure element 118 because it is made of an open cell foam material know to those skilled in the art. Alternatively, treatment composition 230 (FIG. 8) fills only a portion of cartridge reservoir 222 because treatment composition pressure element 218 is an impermeable membrane. The pressure elements of the present invention can be open cell foam, bladders, flexible membranes, solid wax and the like.

Above and below treatment composition pressure element 118 are two unfilled portions of cartridge assembly reservoir 122 which are referred to herein as head spaces, specifically, in FIG. 7 standpipe head space 132 and base head space 134. Both of these head spaces contain treatment composition 130, which can be added to cartridge assembly 112 via optional treatment composition fill port 144 which is sealed with treatment composition fill port plug 146. Fill port 144 and fill port plug 146 are often used in refillable cartridges, why cartridges that are not intended to be refilled might be filled and then sealed without the need for a fill port.

FIG. 8. shows treatment composition pressure element 218 as a flexible membrane situated between cartridge assembly base 216 and the other end defined by standpipe 221 and die 226 comprising nozzles 225. Treatment composition 230 occupies the area between treatment composition pressure element 218 and standpipe 221, and there are no head spaces that contain treatment composition. This brings us to the discussion of treatment composition dispersing devices 120 and 220 in FIGS. 7 and 8, respectively. In FIG. 7, treatment composition dispersing devices 120 can be located in standpipe 121, or in standpipe headspace 132. In FIG. 8, only one dispersing device 220 is shown and it is shown with mixing drive 248.

Figure 4:
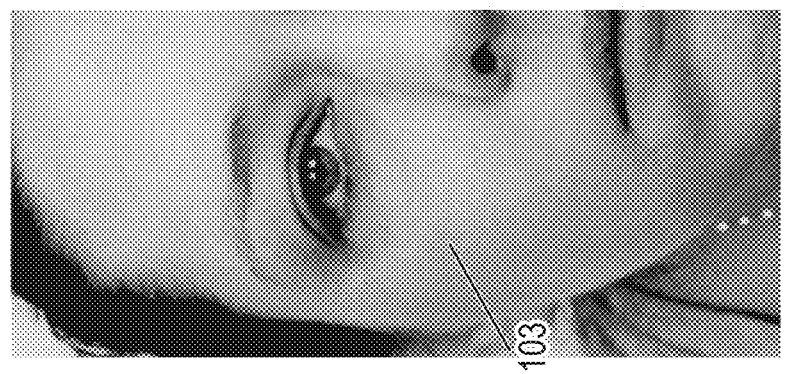
FIG. 4 is the natural, uncovered skin of a female consumer.
Figure 5:
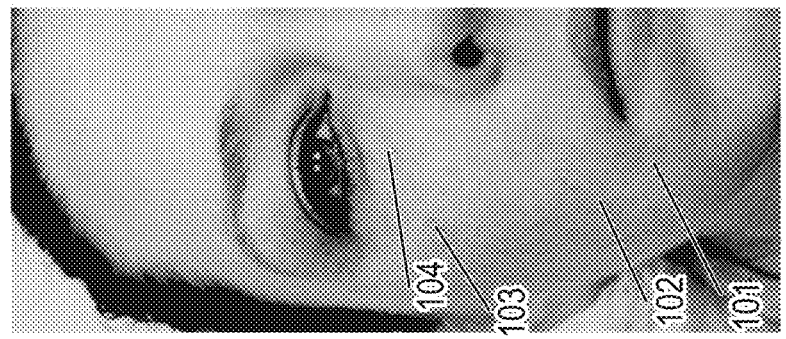
FIG. 5 is the same female consumer in FIG. 4 with applied makeup.
Figure 6:
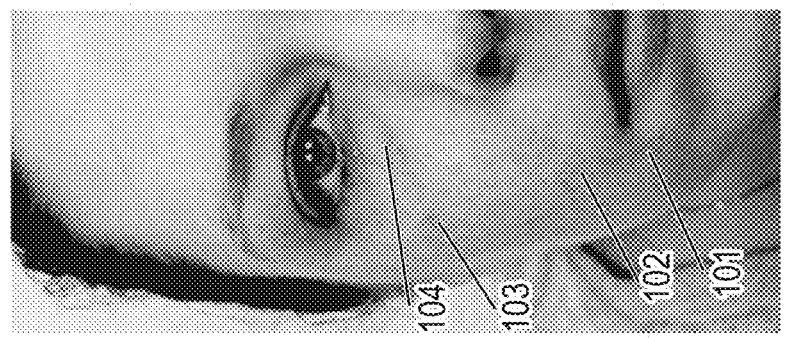
FIG. 6 is the same female consumer as shown in FIG. 4, with no makeup on, after being treated by the methods and apparatuses of the present invention.

Referring now to FIGS. 4, 5 and 6, which are photographs of the same female consumer. FIG. 4 represents her washed, natural, and uncoated skin. FIG. 5 was taken after the subject applied makeup to her face in a manner she would normally do. FIG. 6 was taken after the consumer's makeup was removed and her face treated with the apparatus and methods of this invention. FIGS. 4, 5 and 6 are all taken on the same day, with no appreciable sun exposure between photographs (i.e. the consumer was indoors for the entire treatment period).

Skin deviations 101, 102, 103 and 104 are clear in FIG. 4. After makeup is applied, skin deviations 101, 102, 103 and 104 are all still visible. There are tonal differences on the consumer's skin as well as the skin deviations of FIG. 5 vs. FIG. 4. It is clear from FIGS. 4 and 5 that makeup changes the overall tone of human skin, but does not cover up imperfections.

The consumer washes her face to remove the applied makeup after the photograph of FIG. 5 is taken, and then her skin is treated with the apparatuses and methods of this invention, then the photograph of FIG. 6 is taken. Skin deviations 101, 102 and 104 from FIGS. 4 and 5 are largely invisible in FIG. 6. Skin deviation 103 is barely visible after treatment with the present apparatuses and methods. Accordingly, the present apparatuses and methods provide a substantial and visible change to the appearance of human skin versus the natural condition of the skin and the skin with applied makeup.

Multiple configurations are shown for the dispersing devices of the present invention and others are contemplated for use with the present invention. Essentially, the dispersing devices are used to mix the treatment composition within the limited space of the cartridge assembly reservoir. The dispersing devices can be spherical balls, or irregularly shaped objects. They can be plastic, metal, wood, or generally any other solid, or semi-solid material. Preferably, the material does not dissolve in treatment composition, but even a dispersing device that gradually dissolves could be used herein. The dispersing devices can be free floating as shown in FIG. 7, which relies on movement of the entire cartridge assembly to shake the dispersing elements and subsequently mix the treatment composition. Likewise, the dispersing device can be mechanically moved as shown in FIG. 8, wherein treatment composition dispersing device 220 is rotated by mixing drive 248. Dispersing device 220 can be mechanically affixed to mixing drive 248 or magnetically attached. Mixing drive 248 can rotate (as indicated by the arrows in FIG. 8), it can vibrate, or it can oscillate vertically and/or horizontally.

An "L" shaped baffle 249 is shown in FIG. 8. Baffle 249 takes the treatment composition 230 near and around dispersing device 220 and mixes it thoroughly. The flow of treatment composition 230 (shown by direction flow arrows 250) immediately after being thoroughly mixed by dispersing device 220 and mixing drive 248 passes into standpipe 221. By this method of thorough mixing then immediately supplying the mixed treatment composition to the standpipe, the treatment composition fed to nozzles 225 contains the proper blend of treatment particles and liquid. The general concept of using a baffle to direct the flow of mixed material immediately to the standpipe, can be used with foam core pressure element as shown in FIG. 7 as element 118. Other combinations of treatment composition pressure elements and baffles and dispersing devices are contemplated for use in the present invention.

While numerous examples of how to impart mechanical mixing to the treatment composition are shown, many others are contemplated within the scope of the invention, for example sonic mixing from either within the reservoir, or from a source exterior to the cartridge assembly. It is understood that the vast majority of prior treatment compositions did not comprise particulate matter, thus mechanical mixing was neither necessary nor desired.

Turning now to FIGS. 9-12, which show two different standpipes 321 (FIGS. 9 and 10) and 421 (FIGS. 11 and 12). FIGS. 9 and 10 are two different views of the same cartridge body 314 and cartridge reservoir 322. Standpipe 321 defines a standpipe reservoir 328 which is defined by standpipe wall 324 standpipe base 323. As discussed earlier, standpipe base is a portion of die wall 327 of cartridge body 314. Necessarily, the standpipe reservoir 328 has a volume that can be calculated by standard methods, for example, base times height. Fluid can be used to fill the reservoir and the volume of that fluid measured or weighed, to determine the standpipe volume. Those skilled in the art will be familiar with many ways to determine both the volume of the standpipe as well as the volume of the cartridge reservoir (322 I FIGS. 9 and 10). To achieve the necessary and desired flow of particulate containing treatment compositions through the nozzles of the present invention, the ration of cartridge reservoir to standpipe reservoir, on a volumetric basis is very important. Preferably, the ratio of the cartridge reservoir volume to the standpipe reservoir volume is from about 50:1 to about 3:1, even more preferably from about 20:1 to about 4:1, and more preferably about 8:1. Another way of characterizing the ratio of the cartridge volume to the standpipe volume is by the ratio of the surface area of the die wall to the standpipe base which is preferably from about 1.1:1 to about 3:1. FIGS. 11 and 12 are likewise are two different views of the same cartridge body 414 and cartridge reservoir 422. Standpipe 421 defines a standpipe reservoir 428 which is defined by standpipe wall 424 standpipe base 423. As discussed earlier, standpipe base is a portion of die wall 427 of cartridge body 414.

While inkjet cartridges are shown and exemplified herein, treatment compositions may be applied with other "flow control" devices or non-drop control devices. Flow control devices typically are characterized as "drop control techniques" where individual droplets of the substance are controlled. Ink jet printers, which are known to the art, are examples of drop on demand applicators and this technology is applicable for use in the present invention. Piezo electric drop control devices and other micro electromechanical systems are appropriate for use with the current devices. Spray devices and electrostatic spray devices are non-drop control techniques where droplets are produced and controlled only in aggregate. Often in a spray device, a lack of individual droplet control, or "randomness" is desired in order to produce a smooth application over a relatively large area. By contrast, it is often desirable to provide very specific control of the amount and placement of the treatment compositions.

Examples of drop control include "fine flow control" where the flow of the substance is precisely controlled to deliver droplets as desired; and "inkjet technologies." An older inkjet technology includes supplying a continuous flow of charged droplets past electrostatic deflector plates which are alternately charged so that the plates either permit a droplet to pass or deflect to a gutter. This technique was the original design basis for inkjet printers. Other inkjet technologies include "drop on demand" such as thermal devices provided by Hewlett Packard, and piezoelectric devices such as provided by Epson and other printer manufacturers. In one embodiment of the current invention, the drop on demand technology is combined with charging the droplets.

Equipment that might be useful in constructing an apparatus of the present invention are described in the following published patent applications: WO 2008/098234 A2, Handheld Apparatus and Method for the Automated Application of Cosmetics and Other Surfaces, first filed 11 Feb. 2007; WO 2008/100878 A1, System and Method for Applying a Treatment composition to Change a Person's Appearance Based on a Digital Image, first filed 12 Feb. 2007; WO 2008/098235 A2, System and Method for Providing Simulated Images Through Cosmetic Monitoring, first filed 11 Feb. 2007; WO 2008/100880 A1, System and Method for Applying Agent Electrostatically to Human Skin, first filed 12 Feb. 2007; US 2007/0049832 A1, System and Method for Medical Monitoring and Treatment Through Cosmetic Monitoring and Treatment, first filed 12 Aug. 2005; and US 2007/0035815 A1, System and Method for Applying a Treatment composition to Improve the Visual Attractiveness of Human Skin, first filed 12 Aug. 2005; All six applications filed by Edgar et al. The entire disclosure of each of the six Edgar et al. applications is incorporated herein by reference.

The apparatuses of the present invention are preferably handheld but can be tethered to a structure that moves the apparatus across the keratinous surface to be modified. If handheld, the consumer would simply move the apparatus across the keratinous surface to be treated. Optionally, multiple apparatuses can be configured in a stationary structure wherein the consumer places the keratinous surface to be modified and multiple readings and applications occur simultaneously or in sequence.

The treatment composition can be applied to the keratinous surface by scanning and applying at the same time while making multiple passes over the surface. Several advantages result from using multiple pass application. The process for multiple pass applications is to make a partial application of the treatment composition, then to scan again the area of skin that has received the partial application. A further application of treatment compositions can be made, and still further multiple pass scanning and applications can be made to approach an aesthetic goal. Thus, the consumer can select the end point of the treatment, i.e. the "aesthetic goal", thus tailoring the treatment time to individual needs and preferences. Attempting to make all corrections in one treatment pass has been shown to overcorrect in certain areas.

It may be desirable for the apparatus to treat from about 1.0% to about 10% of the keratinous surface that is read by the sensor with a treatment composition. And the applicator may apply the first treatment composition in droplets having an average diameter of from about from about 0.1 μm to about 50 μm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A stable, particulate containing, printer composition comprising:
   a. one or more particulate suspending agents in a concentration of from about 0.05% to about 5%, by weight, wherein the particulate suspending agent is a polyacrylate or polyacrylate derivative with a counter ion selected from the group consisting of sodium, potassium, ammonium, and mixtures thereof;
   b. one or more particulate compositions, wherein the particles in the particulate composition have a combined Particle Size Distribution D50 in the range of about 200 ηm to about 500 ηm; and
   c. water;
   wherein the one or more particulate compositions has a zeta potential of negative 20 or less, or greater than positive 20;
   wherein the printer composition has a viscosity of less than 10 cP and
   wherein the printer composition can be ejected from a thermal inkjet or piezo inkjet printing system.

2. The printer composition according to claim 1, wherein the particles are present in a concentration of from about 1% to about 30.0%, by weight.

3. The printer composition according to claim 1, wherein the particulate composition comprises $TiO_2$ particles and a second particulate composition which is an iron oxide based colorant particulate composition, another colorant particulate composition, or both.

4. The printer composition according to claim 1, further comprising one or more humectants in a concentration of from about 1.0% to about 50.0%, by weight.

5. The printer composition according to claim 4, wherein the humectant is selected from the group consisting of polyethylene glycol, glycerin, butylene glycol, other glycols, and mixtures thereof.

6. The printer composition according to claim 1, wherein the particles in the particulate composition are selected from the group consisting of titanium dioxide, zinc oxide, aluminum hydroxide, iron oxides, boron nitride, silica, talc, carbon black, and mixtures thereof.

7. The printer composition according to claim 1, wherein less than about 5% by volume of the particles in the particulate composition have a surface treatment that comprises silica.

8. The printer composition according to claim 1, wherein the particles have a refractive index between 1.2 and 5.0.

9. The printer composition according to claim 1, wherein the particles have an elastic modulus of from about 0.1 mPa to about 1000 Pa.

10. The printer composition according to claim 1, wherein the composition has a pH in the range of from about 5 to about 10.

11. The printer composition of claim 1 wherein the one or more particulate compositions have a zeta potential of negative 30 or less, or greater than positive 30.

12. The printer composition of claim 1 wherein the particulate suspending agent is sodium polyacrylate.

13. The printer composition of claim 2 wherein the particles in the particulate composition have a combined Particle Size Distribution D90 of less than about 1 μm.

14. The printer composition of claim 4 comprising one or more humectants in a concentration of from about 1.0% to about 30.0%, by weight.

15. The printer composition of claim 1 wherein the particulate suspending agent has a molecular weight of between about 1,000 and about 20,000.

16. The printer composition of claim 1 wherein the printer composition has a contrast ratio of from about 5 to about 35.

17. The printer composition of claim 12 wherein the printer composition comprises from 0.05 to 0.50%, by weight, of the particulate suspending agent.

* * * * *